US010266868B2

(12) United States Patent
Chakrabarty et al.

(10) Patent No.: US 10,266,868 B2
(45) Date of Patent: Apr. 23, 2019

(54) COMPOSITIONS FOR TREATING HIV INFECTION WITH CUPREDOXIN AND CYTOCHROME C

(75) Inventors: Ananda Chakrabarty, Villa Park, IL (US); Tapas Das Gupta, River Forest, IL (US); Tohru Yamada, Oak Park, IL (US); Anita Chaudhari, Jacksonville, FL (US); Arsenio Fialho, Lisbon (PT); Chang Soo Hong, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 12/880,682

(22) Filed: Sep. 13, 2010

(65) Prior Publication Data

US 2011/0070217 A1    Mar. 24, 2011

Related U.S. Application Data

(62) Division of application No. 12/398,708, filed on Mar. 5, 2009, now Pat. No. 7,795,410, which is a division of application No. 11/943,034, filed on Nov. 20, 2007, now Pat. No. 7,511,117, which is a division of application No. 11/436,591, filed on May 19, 2006, now Pat. No. 7,301,010.

(51) Int. Cl.
*C07K 14/195* (2006.01)
*C12Q 1/18* (2006.01)

(52) U.S. Cl.
CPC .............. *C12Q 1/18* (2013.01); *C07K 14/195* (2013.01); *C07K 2319/00* (2013.01); *G01N 2333/16* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 6,375,925 B1 | 4/2002 | Tsimikas et al. | |
| 6,551,795 B1 | 4/2003 | Rubenfield et al. | |
| 7,301,010 B2 | 11/2007 | Chakrabarty et al. | |
| 7,338,766 B2 | 3/2008 | Chakrabarty et al. | |
| 7,381,701 B2 | 6/2008 | Chakrabarty et al. | |
| 7,511,117 B2 | 3/2009 | Chakrabarty et al. | |
| 2003/0059436 A1 | 3/2003 | Chishti et al. | |
| 2006/0149037 A1 | 7/2006 | Chakrabarty et al. | |
| 2008/0312413 A1 | 12/2008 | Chakrabarty et al. | |

FOREIGN PATENT DOCUMENTS

| WO | 2002076380 A2 | 10/2002 |
|---|---|---|
| WO | 2005018662 A1 | 3/2005 |

OTHER PUBLICATIONS

Bowie et al., Science, 1990, 257:1306-1310.*
Burgess et al., Journal of Cell Biology,1990, 111:2129-2138.*
Lazar et al., Molecular and Cellular Biology, 1988, 8:1247-1252.*
Arvidsson et al., Eur. J. Biochem., 1989, 179:195-200 with sequence alignment.*
Sequence Alignment Rubenfield_SEQ ID No. 1.*
Sequence Alignment Rubenfield_SEQ ID No. 2.*
Trees et al., The Journal of Infectious Diseases, 1990, 161(2):336-339.*
Tramont, Clinical Microbiology Reviews, Apr. 1989, 2(suppl.):S74-S77.*
Hasegawa et al., The Journal of Biological Chemistry, 1999, 274(53):37533-37537.*
Anonymous: "Plastocyanin precursor" Database EMBL, Online, Nov. 1, 1997, XP002306632 abstract.
Anonymous: "Pseudoazurin precursor" Database EMBL, Online, Feb. 1, 1991, XP002306634 abstract.
Anonymous: "Rusticyanin precursor" Database EMBL, Online, Mar. 1, 1992, XP002306633 abstract.
Aplyo et al., Bioche. Biophys. Res. Comm. 332:965-968 (2005).
Buckley, Letter of Nature 397:534-539 (1999).
Canters et al., FEBS Letters 325(1-2):39-48 (1993).
Chakrabarty, J. Bacteriol. 185(9):2683-86, (2003).
Goto et al., Mol Microbiol. 47(2):549-59 (2003).
Gough et al., Structure (Cambridge) 12(6):917-925 (2004).
Hiraoka et al., Proc. Natl. Acad. Sci. 101(17):6427-32 (2004).
Hoitink et al., Gene 90(1):15-20 (1990).
Kamp et al., Bioenergetics 1019(3):283-292 (2000).
Murphy et al., Biochemistry 32:1965-1975 (1993).
Nar et al., FEBS Letters 306(2-3):119-124 (1992).
Punj et al., Biochem. Biophys. Res. Commun. 312(1):109-14 (2003).
Punj et al., Oncogene 23(13):2367-78 (2004).
Punj et al., J. Bacteriol. 185(10):3167-78 (2003).
Yamada et al., Infection and Immunity 70(12):7054-7062 (2002).
Yamada et al., Proc. Natl. Acad. Sci. 101(14):4770-4775 (2004).
Yamada et al., Proc. Natl. Acad. Sci. 99(22):14098-14103 (2002).
Yamada et al., Cell Microbiol. 7(10):1418-1431 (2005).
Yamada et al., Cell Cycle 3(6):752-755 (2004).
Yamada et al., Cell Cycle 3(9):1182-1187 (2004).
Yang et al., Pharmacological Research 52(5):413-421 (2005).

(Continued)

*Primary Examiner* — Nicole Kinsey White
(74) *Attorney, Agent, or Firm* — Benesch, Friedlander, Coplan & Aronoff LLP

(57) ABSTRACT

The present invention relates to cupredoxin, specifically *Pseudomonas aeruginosa* azurin, and/or *Pseudomonas aeruginosa* cytochrome $c_{551}$ and their use in inhibiting of viral infection, and in particular infection of mammalian cells by the Human Immunodeficiency Virus (HIV). The invention also relates to variants and derivatives of cupredoxin and cytochrome c that retain the ability to inhibit viral infection, and in particular infection by the Human Immunodeficiency Virus (HIV). The invention also relates to research methods for studying viral and bacterial infection in mammalian cells.

7 Claims, 3 Drawing Sheets

Specification includes a Sequence Listing.

(56) References Cited

OTHER PUBLICATIONS

Ye et al., Chinese Journal of Cancer 24(3):298-304 (2005).
Zaborina et al., Infect. Immun. 67(10):5231-42 (1999).
Zaborina et al., Microbiology 146(10):2521-30 (2000).
Zaborina, Molecular Microbiology 31(5):1333-1343 (1999).

* cited by examiner

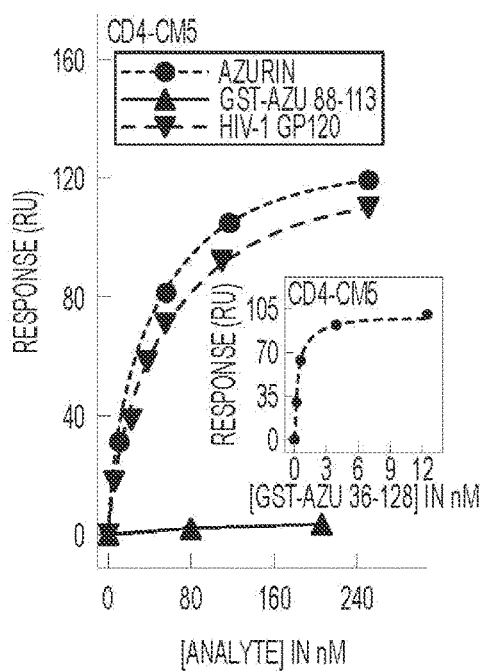
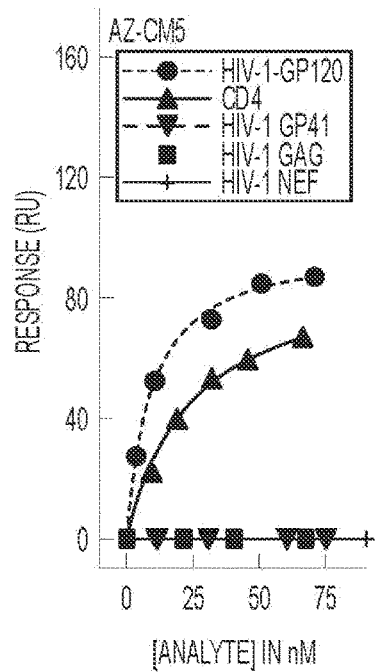
FIG. 2A
FIG. 2B
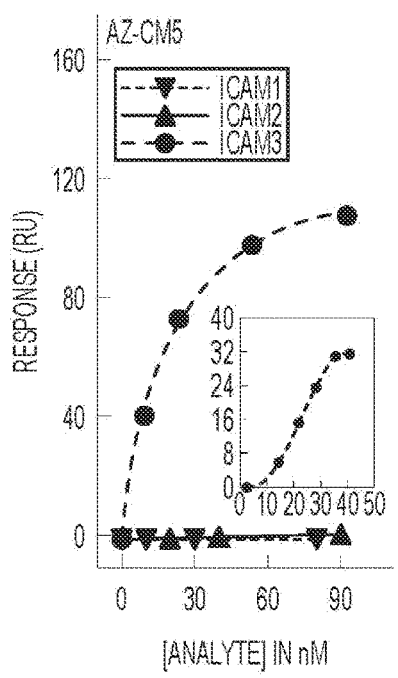
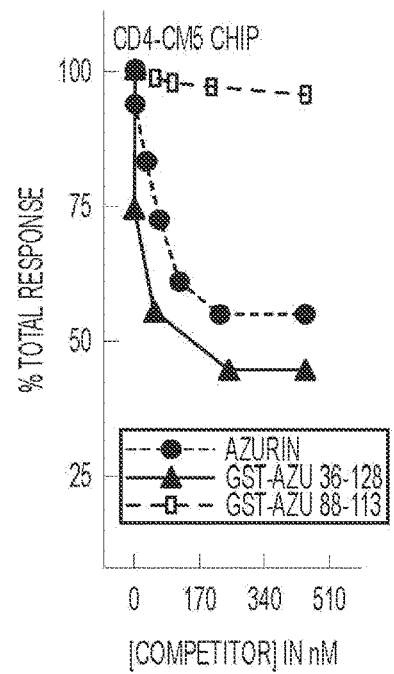
FIG. 2C
FIG. 2D

US 10,266,868 B2

COMPOSITIONS FOR TREATING HIV INFECTION WITH CUPREDOXIN AND CYTOCHROME C

RELATED APPLICATIONS

The present application is a divisional and claims the benefit, under 35 U.S.C. § 120, of U.S. patent application Ser. No. 12/398,708, filed Mar. 5, 2009, issued as U.S. Pat. No. 7,795,410 on Sep. 14, 2010, which is a divisional of U.S. patent Ser. No. 11/943,034, filed Nov. 20, 2007, which issued as U.S. Pat. No. 7,511,117 on Mar. 31, 2009, which is a divisional of U.S. patent application Ser. No. 11/436,591, filed May 19, 2006, which issued as U.S. Pat. No. 7,301,010 on Nov. 27, 2007; and which claims priority under 35 U.S.C. §§ 119 and 120 to co-filed U.S. patent application Ser. No. 11/436,590, entitled "Compositions and Methods for Treating Malaria with Cupredoxins and Cytochrome", filed May 19, 2006, issued as U.S. Pat. No. 7,338,766 on Mar. 4, 2008, which claims priority to U.S. Provisional Patent Application Ser. No. 60/780,868, filed Mar. 10, 2006, and U.S. Provisional Patent Application Ser. No. 60/682,813, filed May 20, 2005; and which is a continuation-in-part of U.S. patent application Ser. No. 11/244,105, filed Oct. 6, 2005, issued as U.S. Pat. No. 7,691,383 issued on Apr. 6, 2010, which claims priority to U.S. Provisional Patent Application Ser. No. 60/616,782, filed Oct. 7, 2004, and U.S. Provisional Patent Application Ser. No. 60/680,500, filed May 13, 2005; and which is a continuation-in-part of U.S. patent application Ser. No. 10/720,603, filed Nov. 24, 2003, issued as U.S. Pat. No. 7,491,394 on Feb. 17, 2009, which claims priority to U.S. Provisional Patent Application Ser. No. 60/414,550, filed Aug. 15, 2003, and which is a continuation-in-part of U.S. patent application Ser. No. 10/047,710, filed Jan. 15, 2002, issued as U.S. Pat. No. 7,084,105 on Aug. 1, 2006, which claims priority to U.S. Provisional Patent Application Ser. No. 60/269,133, filed Feb. 15, 2001. The entire contents of these priori applications is fully incorporated herein by reference.

FIELD OF THE INVENTION

The present invention relates to cupredoxin, specifically *Pseudomonas aeruginosa* azurin, and/or *Pseudomonas aeruginosa* cytochrome $c_{551}$ and their use in inhibiting of viral infection, and in particular infection of mammalian cells by the Human Immunodeficiency Virus (HIV). The invention also relates to variants and derivatives of cupredoxin and cytochrome c that retain the ability to inhibit viral infection, and in particular infection by the Human Immunodeficiency Virus (HIV). The invention also relates to research methods for studying viral and bacterial infection in mammalian cells.

BACKGROUND

While human immunodeficiency virus (HIV) infection, which results in AIDS, is a relatively new infection in the human population, it has quickly risen to the foremost health problem in the world. HIV/AIDS is now the leading cause of death in sub-Saharan Africa, and is the fourth biggest killer worldwide. At the end of 2001, it was estimated that 40 million people were living with HIV infection world wide. The Centers for Disease Control (CDC) estimates that nearly 800,000 people are living with AIDS in the US, and 40,000 new cases diagnosed each year. While better treatment methods are now known to prolong the life of patients with HIV infection, there is still no cure.

Modern anti-HIV drugs target several different stages of the HIV life cycle, and several of the enzymes that HIV requires to replicate and survive. Some of the commonly used anti-HIV drugs include nucleoside reverse transcriptase inhibitors such as AZT, ddI, ddC, d4T, 3TC, and abacavir; nucleotide reverse transcriptase inhibitors such as tenofovir; non-nucleoside reverse transcriptase inhibitors such as nevirapine, efavirenz and delavirdine; protease inhibitors such as saquinavir, ritonavir, indinavir, nelfinavir, amprinavir, lopinavir and atazanavir; and fusion inhibitors such as enfuvirtide. However, in many HIV infected patients, none of these antiviral drugs, alone or in combination, is effective to prevent the progression of chronic infection or treat acute AIDS. The high mutation rate of the HIV virus and associated emergence of HIV strains resistant to drugs is one large factor that results in the inability to effectively treat HIV infection. New and better treatments are required for HIV infection.

SUMMARY OF THE INVENTION

The present invention relates to compositions and methods of use of cupredoxins and/or cytochrome $c_{551}$ and their use to inhibit viral infections in mammalian cells, and in particular HIV infection. Specifically, the present invention relates to compositions comprising the peptides *Pseudomonas aeruginosa* azurin and/or cytochrome $c_{551}$, and/or variants and/or derivatives thereof, and methods to use these compositions and peptides to inhibit the growth of HIV-1 infection in mammalian cells and patients. The invention also relates to variants and derivatives of cupredoxin and cytochrome $c_{551}$ that retain the ability to inhibit the growth of viral infection, and in particular infection by the HIV.

One aspect of the invention is an isolated peptide that is a variant, derivative or structural equivalent of a cupredoxin or cytochrome $c_{551}$ and that can inhibit the growth of HIV-1 infection in mammalian cells. In some embodiments, the cupredoxin is azurin, pseudoazurin, plastocyanin, rusticyanin, Laz or auracyanin, and specifically azurin or Laz. In other embodiments, the cupredoxin is from *Pseudomonas aeruginosa*, *Alcaligenes faecalis*, *Achromobacter xylosoxidan*, *Bordetella bronchiseptica*, *Methylomonas* sp., *Neisseria meningitidis*, *Neisseria gonorrhea*, *Pseudomonas fluorescens*, *Pseudomonas chlororaphis*, *Xylella fastidiosa* or *Vibrio parahaemolyticus*, and specifically *Pseudomonas aeruginosa* or *Neisseria gonorrhea*. In some embodiments, the peptide is part of one of SEQ ID NOS: 1-17. In some embodiments, the peptide has at least about 90% amino acid sequence identity to a sequence in SEQ ID NOS: 1-17.

In some embodiments, the isolated peptide may be a truncation of cupredoxin or cytochrome $c_{551}$. The peptide may be more than about 10 residues and not more than about 100 residues. In some embodiments, the isolated peptide comprises a region of azurin that is residues 36-128, residues 36-88 or residues 88-113. In other embodiments, the isolated peptide consists of a region of azurin that is residues 36-128, residues 36-88 or residues 88-113. In other embodiments, the peptide comprises equivalent residues of a cupredoxin as a region of azurin that is residues 36-128, residues 36-88 and residues 88-113.

Another aspect of the invention is a composition which comprises at least one cupredoxin, cytochrome $c_{551}$, or isolated peptide that is a variant, derivative or structural equivalent of a cupredoxin or cytochrome $c_{551}$ and that can inhibit the growth of HIV-1 infection in mammalian cells, in a pharmaceutical composition. In some embodiments, the pharmaceutical composition is formulated for intravenous administration. In other embodiments, the cupredoxin is from *Pseudomonas aeruginosa, Alcaligenes faecalis, Achromobacter xylosoxidan, Bordetella bronchiseptica, Methylomonas* sp., *Neisseria meningitidis, Neisseria gonorrhea, Pseudomonas fluorescens, Pseudomonas chlororaphis, Xylella fastidiosa* or *Vibrio parahaemolyticus*, and specifically *Pseudomonas aeruginosa* or *Neisseria gonorrhea*. In some embodiments, the cupredoxin or cytochrome $c_{551}$ is selected SEQ ID NOS: 1-17.

Another aspect of the invention is a method to treat a patient infected with a virus or bacteria, comprising administering to the patient a therapeutically effective amount of a composition which comprises at least one cupredoxin, cytochrome c551, or isolated peptide that is a variant, derivative or structural equivalent of a cupredoxin or cytochrome c551 and that can inhibit the growth of HIV-1 infection in mammalian cells, in a pharmaceutical composition. The patient may be infected with HIV-1, Herpes simplex virus (HSV), Ebola virus, cytomeglovirus (CMV), parainfluenza viruses types A, B and C, hepatitis virus A, B, C, and G, the delta hepatitis virus (HDV), mumps virus, measles virus, respiratory syncytial virus, bunyvirus, arena virus, Dhori virus, poliovirus, rubella virus, dengue virus; SIV or *Mycobacterium tuberculosis*, and specifically HIV-1. In some embodiments, the patient is human. In some embodiments, the composition is administered by intravenous injection, intramuscular injection, subcutaneous injection, inhalation, topical administration, transdermal patch, suppository or oral, and specifically by intravenous injection. The composition may be administered within 0 minutes to 1 week of the administration of another anti-HIV drug, specifically at about the same time as another anti viral, anti-bacterial and/or anti-HIV drug.

Another aspect of the invention is a composition comprising at least two of an isolated cupredoxin, a cytochrome c551, and variant, derivative or structural equivalent of a cupredoxin or a cytochrome c551. In some embodiments, the composition is in a pharmaceutical composition.

Another aspect of the invention is a kit comprising the composition comprising at least one cupredoxin, cytochrome c551, or isolated peptide that is a variant, derivative or structural equivalent of a cupredoxin or cytochrome c551 and that can inhibit the growth of HIV-1 infection in mammalian cells in a pharmaceutical composition in a vial. In some embodiments, the kit is designed for intravenous administration.

Another aspect of the invention is a method to study viral and bacterial infection in mammalian cells, comprising the steps of contacting the cells with a cupredoxin or cytochrome c551, or variant, derivative or structural equivalent thereof; contacting the cells with a bacteria or virus; and measuring the growth of infection of the virus or bacteria. In some embodiments, the step of contacting the cells with a cupredoxin or cytochrome c551, or variant, derivative or structural equivalent thereof occurs before the step of contacting the cells with a bacteria or virus. In other embodiments, the step of contacting the cells with a cupredoxin or cytochrome c551, or variant, derivative or structural equivalent thereof occurs after the step of contacting the cells with a bacteria or virus. In some embodiments, the cells are human cells. In other embodiments, the cells are lymphoma cells or peripheral blood mononuclear cells. In other embodiments, the virus or bacteria is HIV-1, Herpes simplex virus (HSV), Ebola virus, cytomeglovirus (CMV), parainfluenza viruses types A, B and C, hepatitis virus A, B, C, and G, the delta hepatitis virus (HDV), mumps virus, measles virus, respiratory syncytial virus, bunyvirus, arena virus, Dhori virus, poliovirus, rubella virus, dengue virus, SIV and *Mycobacterium tuberculosis*, specifically HIV-1.

Another aspect of the invention is an expression vector, which encodes peptide that is a variant, derivative or structural equivalent of a cupredoxin or cytochrome c551 and that can inhibit the growth of HIV-1 infection in mammalian cells.

These and other aspects, advantages, and features of the invention will become apparent from the following figures and detailed description of the specific embodiments.

BRIEF DESCRIPTION OF THE SEQUENCES

SEQ ID NO: 1. Amino acid sequence of azurin from *Pseudomonas aeruginosa*.

SEQ ID NO: 2. Amino acid sequence of cytochrome c551 from *Pseudomonas aeruginosa*.

SEQ ID NO: 3. Amino acid sequence of plastocyanin from *Phormidium laminosum*.

SEQ ID NO: 4. Amino acid sequence of rusticyanin from *Thiobacillus ferrooxidans*.

SEQ ID NO: 5. Amino acid sequence of pseudoazurin from *Achromobacter cycloclastes*.

SEQ ID NO: 6. Amino acid sequence of azurin from *Alcaligenes faecalis*.

SEQ ID NO: 7. Amino acid sequence of azurin from *Achromobacter xylosoxidans* ssp. *denitrificans* I.

SEQ ID NO: 8. Amino acid sequence of azurin from *Bordetella bronchiseptica*.

SEQ ID NO: 9. Amino acid sequence of azurin from *Methylomonas* sp. J.

SEQ ID NO: 10. Amino acid sequence of azurin from *Neisseria meningitidis* Z2491.

SEQ ID NO: 11. Amino acid sequence of azurin from *Pseudomonas fluorescen*.

SEQ ID NO: 12. Amino acid sequence of azurin from *Pseudomonas chlororaphis*.

SEQ ID NO: 13. Amino acid sequence of azurin from *Xylella fastidiosa* 9a5c.

SEQ ID NO: 14. Amino acid sequence of stellacyanin from *Cucumis sativus*

SEQ ID NO: 15. Amino acid sequence of auracyanin A from *Chloroflexus aurantiacus*

SEQ ID NO: 16. Amino acid sequence of auracyanin B from *Chloroflexus aurantiacus*

SEQ ID NO: 17. Amino acid sequence of cucumber basic protein from *Cucumis sativus*.

SEQ ID NO: 18 is the amino acid sequence of the H.8 region from Laz from *Neisseria gonorrhoeae* F62.

SEQ ID NO: 19 is the amino acid sequence of Laz from *Neisseria gonorrhoeae* F62.

SEQ ID NO: 20 is the forward primer to PCR amplify the Laz-encoding gene (laz) of *Neisseria gonorrhoeae*.

SEQ ID NO: 21 is the reverse primer to PCR amplify the Laz-encoding gene (laz) of *Neisseria gonorrhoeae*.

SEQ ID NO: 22 is the forward primer to PCR amplify a 3.1 kb fragment of pUC18-laz.

SEQ ID NO: 23 is the reverse primer to PCR amplify a 3.1 kb fragment of puc18-laz.

SEQ ID NO: 24 is the forward primer to PCR amplify a 0.4 kb fragment of pUC19-paz.

SEQ ID NO: 25 is the reverse primer to PCR amplify a 0.4 kb fragment of pUC19-paz.

SEQ ID NO: 26 is the forward primer for pGST-azu 36-128.

SEQ ID NO: 27 is the reverse primer for pGST-azu 36-128.

SEQ ID NO: 28 is the forward primer for pGST-azu 36-89.

SEQ ID NO: 29 is the reverse primer for pGST-azu 36-89.

SEQ ID NO: 30 is the forward primer for pGST-azu 88-113.

SEQ ID NO: 31 is the reverse primer for pGST-azu 88-113.

SEQ ID NO: 32 is an oligonucleotide for site directed mutagenesis for the preparation of pGST-azu 88-113.

SEQ ID NO: 33 is an oligonucleotide for site directed mutagenesis for the preparation of pGST-azu 88-113.

BRIEF DESCRIPTION OF THE FIGURES

FIG. 2 depicts surface plasmon resonance binding curves depicting the binding patterns of cupredoxins with CD4 and HIV-1 gp120. (A) SPR titration curves showing novel and specific binding of azurin, and GST-Azu 36-128 (shown as an inset) with immobilized CD4 on carboxymethyldextran coated gold sensor chips (CD4-CB5). HIV-1 gp120, HIV-1 gag, and HIV-1 nef served as the positive and negative controls respectively. Relative binding affinities were determined via fitting the data to $R_{eq}=R_{max}/(1+(K_d/C))$ with the curve fits connecting the data points above. The CD4 binding $K_d$ values are: 36.9±2.0 nM (azurin), 0.34±0.04 nM (GST-Azu 36-128), and 48.1±3.1 nM (HIV-1 gp120). (B) The binding titrations when immobilized azurin (Az-CM5) is in contact with HIV proteins. Due to large nonspecific binding to the bare Au-CM5 chip, CM5 was added as an eluent to the running buffer (1 mg/ml CM5 to HBS-EP buffer). Curve fits gave Kd's of 25.1±3.1 nM (CD4), and 8.9±0.8 nM (HIV-1 gp120). (C) SPR curves for the binding of ICAMs (ICAM-1, ICAM-2, ICAM-3 and NCAM, inset) with immobilized azurin were determined under similar conditions as for experiments in part (B). The selective recognition of azurin with ICAM-3, but not with ICAM-1 or ICAM-2, is notable and the binding strength was 19.5±5.4 nM. The Kd for NCAM binding with azurin, as shown in the inset, was 20±5.0 nM. (D) SPR binding competition studies with CD4 immobilized on CM5 sensor chips. Azurin+HIV-1 gp120 solutions were added at different azurin concentrations (0-4500 nM, [HIV-1 gp120] is 242 nM) to the sensor surface and the data were plotted as a ratio of resonances, % total response $[R_{eq}$ (azurin+HIV-1 gp120)/$(R_{eq}/$(HIV-120))]. GST-Azu 36-128 was titrated with HIV-1 gp120 to immobilized CD4 and analyzed in a similar manner. Competition data suggests 1:1 stoichiometry of binding between azurin and GST-Azu 36-128 with immobilized CD4.

DETAILED DESCRIPTION OF THE INVENTION

Definitions

Figure 1:
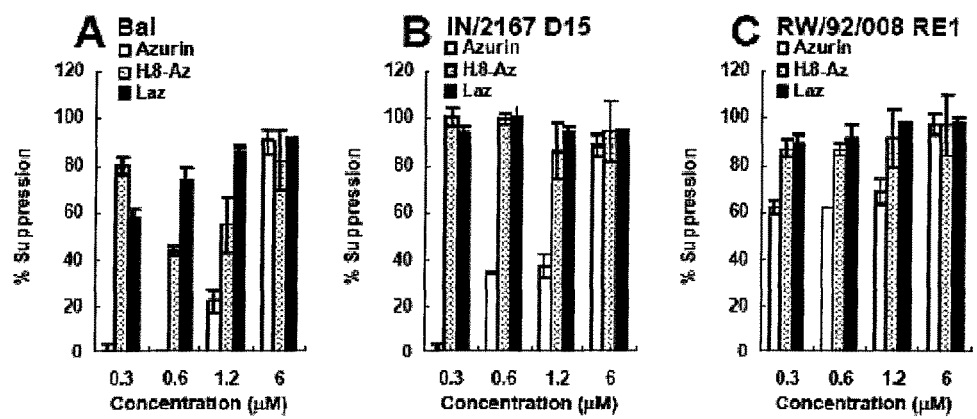
FIG. 1 depicts the inhibition of HIV-1 viral growth by azurin, H.8-azurin (H.8-Az) and Laz. These three proteins were incubated at different concentrations with PBMC followed by addition of the three subtypes of HIV-1. After 2 h incubation, the virus was removed but the proteins added back as described in Example 3. Suppression of virus growth was determined by ELISA assays of p24.

As used herein, the term "cell" includes both the singular or the plural of the term, unless specifically described as a "single cell."

As used herein, the terms "polypeptide," "peptide," and "protein" are used interchangeably to refer to a polymer of amino acid residues. The terms apply to amino acid polymers in which one or more amino acid residue is an artificial chemical analogue of a corresponding naturally occurring amino acid. The terms also apply to naturally occurring amino acid polymers. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well.

As used herein, the term "pathological condition" includes anatomic and physiological deviations from the normal that constitute an impairment of the normal state of the living animal or one of its parts, that interrupts or modifies the performance of the bodily functions, and is a response to various factors (as malnutrition, industrial hazards, or climate), to specific infective agents (as worms, parasitic protozoa, bacteria, or viruses), to inherent defects of the organism (as genetic anomalies), or to combinations of these factors.

As used herein, the term "condition" includes anatomic and physiological deviations from the normal that constitute an impairment of the normal state of the living animal or one of its parts, that interrupts or modifies the performance of the bodily functions.

As used herein, the term "suffering from" includes presently exhibiting the symptoms of a pathological condition, having a pathological condition even without observable symptoms, in recovery from a pathological condition, or recovered from a pathological condition.

A used herein, the term "treatment" includes preventing, lowering, stopping, or reversing the progression or severity of the condition or symptoms associated with a condition being treated. As such, the term "treatment" includes medical, therapeutic, and/or prophylactic administration, as appropriate.

As used herein, the term "inhibit the growth of HIV infection" means any means by which HIV infection is decreased, or prevented from increasing in the human body. These means can include, but are not limited to, inhibition of replication of the HIV genome, inhibition of synthesis and/or assembly of the HIV coat proteins, and inhibition of HIV entry into uninfected cells. This definition includes any the method of action of any of the currently known HIV therapies. One method to determine if the growth of HIV infection is inhibited in found in Example 3.

A "therapeutically effective amount" is an amount effective to prevent or slow the development of, or to partially or totally alleviate the existing symptoms in a particular condition for which the subject being treated. Determination of a therapeutically effective amount is well within the capability of those skilled in the art.

The term "substantially pure", when used to modify the term a polypeptide or other compound, as used herein, refers to a polypeptide or compound, for example, a polypeptide isolated from the growth medium, in a form substantially free of, or unadulterated by, active inhibitory agents. The term "substantially pure" refers to a compound in an amount of at least about 75%, by dry weight, of isolated fraction, or "75% substantially pure." More specifically, the term "substantially pure" refers to a compound of at least about 85%, by dry weight, active compound, or "85% substantially pure." Most specifically, the term "substantially pure" refers to a compound of at least about 95%, by dry weight, active compound, or "95% substantially pure." The substantially pure cupredoxin or cytochrome c551 or a variant or derivative thereof can be used in combination with one or more other substantially pure compounds, or another isolated cupredoxin or cytochrome c551.

The phrases "isolated," "purified" or "biologically pure" refer to material which is substantially or essentially free from components which normally accompany the material as it is found in its native state. Thus, isolated peptides in accordance with the invention preferably do not contain materials normally associated with the peptides in their in situ environment. An "isolated" region refers to a region that does not include the whole sequence of the polypeptide from which the region was derived. An "isolated" nucleic acid, protein, or respective fragment thereof has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in substantially pure quantities.

The term "variant" as used herein with respect to a peptide, refers to amino acid sequence variants which may have amino acids replaced, deleted, or inserted as compared to the wild-type polypeptide. Variants may be truncations of the wild-type peptide. Thus, a variant peptide may be made by manipulation of genes encoding the polypeptide. A variant may be made by altering the basic composition or characteristics of the polypeptide, but not at least some of its fundamental activities. For example, a "variant" of azurin can be a mutated azurin that retains its ability to inhibit the growth of HIV infection in mammalian cells. In some cases, a variant peptide is synthesized with non-natural amino acids, such as ε-(3,5-dinitrobenzoyl)-Lys residues. (Ghadiri & Fernholz, J. Am. Chem. Soc., 112:9633-9635 (1990)) In some embodiments, the variant has not more than 20 amino acids replaced, deleted or inserted compared to wild-type peptide. In some embodiments, the variant has not more than 15 amino acids replaced, deleted or inserted compared to wild-type peptide. In some embodiments, the variant has not more than 10 amino acids replaced, deleted or inserted compared to wild-type peptide. In some embodiments, the variant has not more than 6 amino acids replaced, deleted or inserted compared to wild-type peptide. In some embodiments, the variant has not more than 5 amino acids replaced, deleted or inserted compared to wild-type peptide. In some embodiments, the variant has not more than 3 amino acids replaced, deleted or inserted compared to wild-type peptide.

The term "amino acid," as used herein, means an amino acid moiety that comprises any naturally-occurring or non-naturally occurring or synthetic amino acid residue, i.e., any moiety comprising at least one carboxyl and at least one amino residue directly linked by one, two three or more carbon atoms, typically one (a) carbon atom.

The term "derivative" as used herein with respect to a peptide refers to a peptide that is derived from the subject peptide. A derivation includes chemical modifications of the peptide such that the peptide still retains some of its fundamental activities. For example, a "derivative" of azurin can, for example, be a chemically modified azurin that retains its ability to inhibit the growth of HIV infection in mammalian cells. Chemical modifications of interest include, but are not limited to, amidation, acetylation, sulfation, polyethylene glycol (PEG) modification, phosphorylation or glycosylation of the peptide. In addition, a derivative peptide maybe a fusion of a polypeptide or fragment thereof to a chemical compound, such as but not limited to, another peptide, drug molecule or other therapeutic or pharmaceutical agent or a detectable probe.

The term "percent (%) amino acid sequence identity" is defined as the percentage of amino acid residues in a polypeptide that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. In a specific embodiment, Blastp (available from the National Center for Biotechnology Information, Bethesda Md.) is used using the default parameters of long complexity filter, expect 10, word size 3, existence 11 and extension 1.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\% \text{ amino acid sequence identity} = X/Y * 100$$

where
X is the number of amino acid residues scored as identical matches by the sequence alignment program's or algorithm's alignment of A and B and
Y is the total number of amino acid residues in B.

If the length of amino acid sequence A is not equal to the length of amino acid sequence B, the % amino acid sequence identity of A to B will not equal the % amino acid sequence identity of B to A. When comparing longer sequences to shorter sequences, the shorter sequence will be the "B" sequence. For example, when comparing truncated peptides to the corresponding wild-type polypeptide, the truncated peptide will be the "B" sequence.

General

The present invention provides compositions comprising cupredoxin and/or cytochrome $c_{551}$ and methods to inhibit viral and bacterial infection in mammalian cells and in mammalian patients. The present invention specifically relates to compositions comprising cupredoxin and/or cytochrome $c_{551}$, and their use in inhibiting the growth of Human Immunodeficiency Virus (HIV) infection. The invention also relates to variants, derivatives and structural equivalents of cupredoxin and cytochrome $c_{551}$ that retain the ability to inhibit the growth of viral infection, and in particular infection by the HIV, and compositions comprising the same. Most particularly, the invention provides compositions comprising Pseudomonas aeruginosa azurin and cytochrome $c_{551}$, variants, derivatives and structural equivalents of azurin and cytochrome $c_{551}$, and their use to treat patients with viral or bacterial infection, and specifically HIV-1 infection, or prevent infection in those at risk thereof. Finally, the invention provides methods to study infection of mammalian cells by viruses or bacteria by contacting the cells with cupredoxin or cytochrome $c_{551}$, or variant, derivative or structural equivalent thereof before or after the cells are infected, and measuring the growth of infection.

Previously, it was know that two redox proteins elaborated by Pseudomonas aerugisnosa, the cupredoxin azurin and cytochrome $c_{551}$ (cyt $c_{551}$), both selectively enter J774 cells and show significant cytotoxic activity towards these cancerous cells but not normal cells. (Zaborina et al., Microbiology 146: 2521-2530 (2000).) Azurin can also selectively enter human melanoma UISO-Mel-2 or human breast cancer MCF-7 cells. (Yamada et al., PNAS 99:14098-14103 (2002); Punj et al., Oncogene 23:2367-2378 (2004).) Azurin from P. aeruginosa preferentially enters J774 murine reticulum cell sarcoma cells, forms a complex with and stabilizes the tumor suppressor protein p53, enhances the intracellular concentration of p53, and induces apoptosis. (Yamada et al., Infection and Immunity 70:7054-7062 (2002).)

Surprisingly, it is now known that azurin can induce about a 90% suppression of growth of HIV-1 in peripheral blood mononuclear cell (PBMC) cultures. See, Example 3. Azurin is now known to inhibit the growth of three strains of HIV-1, Bal (the most predominant clade B circulating in the US and Western Europe), a clade B African isolate RW/92/008/RE1, and a clade C Indian isolate IN/2167 D15. See, Example 3. Additionally, a cupredoxin-like protein from Neisseria, Laz, is now also known to inhibit the growth of these three HIV-1 strains, as well as a fusion of the H.8 region of the Laz protein with P. aeruginosa azurin. See, Example 3. Finally, it is now known that M44KM64E mutant of azurin and cytochrome c551 from P. aeruginosa can inhibit HIV infection in HIV-infected human blood lymphocytes. See, Example 1.

It is now known that azurin from Pseudomonas aeruginosa has a structural similarly with ICAM-1 (found in HIV-1 particles and known to enhance HIV-1 infectivity), ICAM-2, and CD4 (the primary cell surface receptor for HIV-1). See, Example 2. Surface plasmon resonance experiments have now revealed that in vitro azurin shows significant binding to the cell surface receptor CD4, and surprisingly a higher affinity for CD4 than the HIV-1 surface ligand gp120. See, Example 4. Further, GST-Azu 36-128, a glutathione S-transferase (GST) fusion to azurin amino acids 36-128, showed stronger binding to CD4 than azurin itself, while GST-Azu 88-113 showed no binding to CD4, suggesting that only a part of the azurin protein is responsible for binding to CD4. See, Example 4. Gp120 showed a somewhat stronger binding to azurin than CD4, indicating that azurin binds both gp120 and CD4. Further, ICAM-3 and NCAM showed strong binding the azurin in vitro in surface plasmon resonance assays. See, Example 5. Finally, azurin is now known to bind another receptor of HIV-1, dendritic cell-specific adhesion receptor (DC-SIGN). See, Example 7. Other proteins implicated in HIV-1 entry into host cells, such as gp41, did not show any binding to azurin. See, Example 4.

Through competition experiments, it is now known that azurin can interfere with gp120 binding with its cognate receptor CD4 in vitro. Specifically, GST-Azu 36-128 showed significant ability to compete with gp120 for CD4 binding, and GST-Azu 88-113 showed little ability to compete. See, Example 6. Laz, an azurin like protein from Neisseria, is now know to inhibit the growth of HIV-1 infection in PBMC culture by 73% if added before HIV-1 infection, and very little if added after HIV-1 infection. See, Example 8. While not limiting the operation of the invention to any one mechanism, it now appears that azurin may inhibit the growth of HIV-1 infection in peripheral blood mononuclear cells by interfering with the interaction between the HIV and cell surface receptors such as ICAMs, CD4 and DC-SIGN, to prevent HIV from entering the cell and infecting it.

Accordingly, due to the high degree of structural similarity between cupredoxins, that other cupredoxins will as well inhibit the growth of HIV-1 infection in mammalian blood cells. It follows that in addition to HIV infection, cupredoxins also will suppress other infections of viruses that bind to cell surface receptors similar in structure to the ICAMs, DC-SIGN and CD4. For example, DC-SIGN is also a binding receptor of other viral and bacterial pathogens, including hepatitis C virus (HCV), Ebola virus, cytomeglovirus (CMV) and Mycobacterium tuberculosis. (Wang et al., Chin. Med. J. 117:1395-1400 (2004))

Compositions of the Invention

The invention provides for peptides that are variants, derivatives or structural equivalents of cupredoxin or Pseudomonas aeruginosa cytochrome $c_{551}$. In some embodiments, the peptide is substantially pure. In other embodiments, the peptide is in a composition that comprises or consists essentially of the peptide. In other embodiments, the peptide is isolated. In some embodiments, the peptide is less that a full length cupredoxin or cytochrome $c_{551}$, and retains some of the functional characteristics of the cupredoxin or cytochrome $c_{551}$. In some embodiments, the peptide retains the ability to inhibit the growth of viral or bacterial infection, and more specifically HIV-1 infection in peripheral blood mononuclear cells. In a specific embodiment, the cytochrome $c_{551}$ is SEQ ID NO: 2. In another specific embodiment, the peptide does not raise an immune response in a mammal, and more specifically a human. The invention also provides compositions comprising at least one peptide that is a cupredoxin, Pseudomonas aeruginosa cytochrome $c_{551}$, or variant, derivative or structural equivalent of a cupredoxin or cytochrome $c_{551}$. The invention also provides compositions comprising at least one peptide that is a cupredoxin, Pseudomonas aeruginosa cytochrome $c_{551}$, or variant, derivative or structural equivalent of a cupredoxin or cytochrome $c_{551}$ in a pharmaceutical composition.

Because of the high structural homology between the cupredoxins, it is contemplated that other cupredoxins will have the same anti-HIV activity as Pseudomonas aeruginosa azurin with regards to inhibition of growth of HIV-1 infection. In some embodiments, the cupredoxin is, but is not limited to, azurin, pseudoazurin, plastocyanin, rusticyanin or auracyanin. In particularly specific embodiments, the azurin is derived from *Pseudomonas aeruginosa*, *Alcaligenes faecalis*, *Achromobacter xylosoxidans* ssp. *denitrificans* I, *Bordetella bronchiseptica*, *Methylomonas* sp., *Neisseria meningitidis* Z2491, *Neisseria gonorrhea*, *Pseudomonas fluorescens*, *Pseudomonas chlororaphis*, *Xylella fastidiosa* 9a5 or *Vibrio parahaemolyticus*. In a very specific embodiment, the azurin is from *Pseudomonas aeruginosa*. In other specific embodiments, the cupredoxin comprises an amino acid sequence that is SEQ ID NO: 1, 3-17. In other specific embodiments, the cupredoxin is the Laz protein from *Neisseria meningitidis* or *Neisseria gonorrhea*.

The invention provides for amino acid sequence variants of a cupredoxin or cytochrome $c_{551}$ which have amino acids replaced, deleted, or inserted as compared to the wild-type polypeptide. Variants of the invention may be truncations of the wild-type polypeptide. In some embodiments, the composition comprises a peptide that consists of a region of a cupredoxin or cytochrome $c_{551}$ that is less that the full length wild-type polypeptide. In some embodiments, the composition comprises a peptide that consists of more than about 10 residues, more than about 15 residues or more than about 20 residues of a truncated cupredoxin or cytochrome $c_{551}$. In some embodiments, the composition comprises a peptide that consists of not more than about 100 residues, not more than about 50 residues, not more than about 40 residues or not more than about 30 residues of a truncated cupredoxin or cytochrome $c_{551}$. In some embodiments, composition comprises a peptide to which a cupredoxin or cytochrome $c_{551}$, and more specifically to SEQ ID NOS: 1-17 has at least about 90% amino acid sequence identity, at least about 95% amino acid sequence identity or at least about 99% amino acid sequence identity.

In specific embodiments, the variant of cupredoxin comprises *P. aeruginosa* azurin residues 36-128, azurin residues 36-88, or azurin residues 88-113. In other embodiments, the variant of cupredoxin consists of *P. aeruginosa* azurin residues 36-128, azurin residues 36-88, or azurin residues 88-113. In other specific embodiments, the variant consists of the equivalent residues of a cupredoxin other that azurin. It is also contemplated that other cupredoxin variants can be designed that have a similar activity to azurin residues 36-128, azurin residues 36-88, or azurin residues 88-113. To do this, the subject cupredoxin amino acid sequence will be aligned to the *Pseudomonas aeruginosa* azurin sequence using BLAST, BLAST2, ALIGN2 or Megalign (DNASTAR), the relevant residues located on the *P. aeruginosa* azurin amino acid sequence, and the equivalent residues found on the subject cupredoxin sequence, and the equivalent truncated peptide thus designed.

The variants also include peptides made with synthetic amino acids not naturally occurring. For example, non-naturally occurring amino acids may be integrated into the variant peptide to extend or optimize the half-life of the composition in the bloodstream. Such variants include, but are not limited to, D,L-peptides (diastereomer), (Futaki et al., J. Biol. Chem. 276(8):5836-40 (2001); Papo et al., Cancer Res. 64(16):5779-86 (2004); Miller et al, Biochem. Pharmacol. 36(1):169-76, (1987)); peptides containing unusual amino acids (Lee et al., J. Pept. Res. 63(2):69-84 (2004)), and olefin-containing non-natural amino acid followed by hydrocarbon stapling (Schafmeister et al., J. Am. Chem. Soc. 122:5891-5892 (2000); Walenski et al., Science 305:1466-1470 (2004)) and peptides comprising ε-(3,5-dinitrobenzoyl)-Lys residues.

In other embodiments, the peptide of the invention is a derivative of a cupredoxin or cytochrome $c_{551}$. The derivatives of cupredoxin/or cytochrome $c_{551}$ are chemical modifications of the peptide such that the peptide still retains some of its fundamental activities. For example, a "derivative" of azurin can be a chemically modified azurin that retains its ability to inhibit the growth of HIV infection in mammalian cells. Chemical modifications of interest include, but are not limited to, amidation, acetylation, sulfation, polyethylene glycol (PEG) modification, phosphorylation and glycosylation of the peptide. In addition, a derivative peptide maybe a fusion of a cupredoxin or cytochrome $c_{551}$, or variant, derivative or structural equivalent thereof to a chemical compound, such as but not limited to, another peptide, drug molecule or other therapeutic or pharmaceutical agent or a detectable probe. Derivatives of interest include chemical modifications by which the half-life in the bloodstream of the peptides and compositions of the invention can be extended or optimized, such as by several methods well known to those in the art, including but not limited to, circularized peptides (Monk et al., BioDrugs 19(4):261-78, (2005); DeFreest et al., J. Pept. Res. 63(5): 409-19 (2004)), N- and C-terminal modifications (Labrie et al., Clin. Invest. Med. 13(5):275-8, (1990)), and olefin-containing non-natural amino acid followed by hydrocarbon stapling (Schafmeister et al., J. Am. Chem. Soc. 122:5891-5892 (2000); Walenski et al., Science 305:1466-1470 (2004)).

It is contemplated that the peptides of the composition of invention may be a variant, derivative and/or structural equivalent of a cupredoxin or cytochrome c551. For example, the peptides may be a truncation of azurin that has been PEGylated, thus making it both a variant and a derivative. In one embodiment, the peptides of the invention are synthesized with α,α-disubstituted non-natural amino acids containing olefin-bearing tethers, followed by an all-hydrocarbon "staple" by ruthenium catalyzed olefin metathesis. (Scharmeister et al., J. Am. Chem. Soc. 122:5891-5892 (2000); Walensky et al., Science 305:1466-1470 (2004)) Additionally, peptides that are structural equivalents of azurin may be fused to other peptides, thus making a peptide that is both a structural equivalent and a derivative. These examples are merely to illustrate and not to limit the invention. Variants, derivatives or structural equivalents of cupredoxin or cytochrome $c_{551}$ may or may not bind copper.

In another embodiment, the peptide is a structural equivalent of a cupredoxin or cytochrome $c_{551}$. Examples of studies that determine significant structural homology between cupredoxins and other proteins include Toth et al. (*Developmental Cell* 1:82-92 (2001)). Specifically, significant structural homology between a cupredoxin and the structural equivalent is determined by using the VAST algorithm (Gibrat et al., Curr Opin Struct Biol 6:377-385 (1996); Madej et al., Proteins 23:356-3690 (1995)). In specific embodiments, the VAST p value from a structural comparison of a cupredoxin to the structural equivalent is less than about $10^{-3}$, less than about $10^{-5}$, or less than about $10^{-7}$. In other embodiments, significant structural homology between a cupredoxin and the structural equivalent is determined by using the DALI algorithm (Holm & Sander, J. Mol. Biol. 233:123-138 (1993)). In specific embodiments, the DALI Z score for a pairwise structural comparison is at least about 3.5, at least about 7.0, or at least about 10.0.

In some embodiments, the cupredoxin or cytochrome $c_{551}$, or variant, derivative or structural equivalent thereof has some of the functional characteristics of the *P. aeruginosa* azurin or cytochrome $c_{551}$. In a specific embodiment, the cupredoxin or cytochrome $c_{551}$ inhibits the growth of viral or bacterial infection, and specifically HIV infection in mammalian cells, more specifically in peripheral blood mononuclear cells infected with HIV. The invention also provides for the variants, derivatives and structural equivalents of cupredoxin and cytochrome $c_{551}$ that retain the ability to inhibit the growth of viral or bacterial infection, and specifically HIV infection in mammalian cells. The growth of HIV-1 infection in the cells may be determined by measuring the change in the production of HIV-1 p24 antigen in the cell culture supernatant by a commercial p24 enzyme immunoassay (PerkinElmer Life Sciences, Inc., Wellseley, Mass.). Inhibition of a growth of infection is any decrease or lessening of the rate of increase of that infection that is statistically signification as compared to control treatments.

Because it is now known that cupredoxins and cytochrome $c_{551}$ can limit the growth of viral or bacterial infection, and specifically infection in HIV-infected mammalian cells, it is now possible to design variants and derivatives of cupredoxins that retain this anti-viral or anti-bacterial, and specifically anti-HIV activity. Such variants and derivatives can be made by, for example, creating a "library" of various variants and derivatives of cupredoxins and cytochrome $c_{551}$, and then testing each for anti-viral or anti-bacterial, and specifically anti-HIV activity using one of many methods known in the art, such the exemplary method in Example 3. It is contemplated that the resulting variants and derivatives of cupredoxins with anti-viral or anti-bacterial, and specifically anti-HIV activity can be used in the methods of the invention, in place of or in addition to cupredoxins or cytochrome $c_{551}$.

In some specific embodiments, the cupredoxin or cytochrome, or variant, derivative or structural equivalent thereof binds to CD4 with a binding constant that is statistically different a non-binding control protein. A peptide can be tested for this activity by using surface plasmon resonance analysis as described in Example 4. Other methods to determine whether one protein binds to another are well known in the art and may be used as well.

In some specific embodiments, the cupredoxin or cytochrome, or variant, derivative or structural equivalent thereof binds to gp120 with a binding constant that is statistically different a non-binding control protein. A peptide can be tested for this activity by using surface plasmon resonance analysis as described in Example 4. Other methods to determine whether one protein binds to another are well known in the art and may be used as well.

In some specific embodiments, the cupredoxin or cytochrome, or variant, derivative or structural equivalent thereof binds to ICAM3 with a binding constant that is statistically different a non-binding control protein. A peptide can be tested for this activity by using surface plasmon resonance analysis as described in Examples 4 and 5. Other methods to determine whether one protein binds to another are well known in the art and may be used as well.

In some specific embodiments, the cupredoxin or cytochrome, or variant, derivative or structural equivalent thereof binds to DC-SIGN with a binding constant that is statistically different a non-binding control protein. A peptide can be tested for this activity by using surface plasmon resonance analysis as described in Examples 4 and 5. Other methods to determine whether one protein binds to another are well known in the art and may be used as well.

In some specific embodiments, the peptide of the invention induces apoptosis in a mammalian cancer cell, more specifically a J774 cell. The ability of a cupredoxin or other polypeptide to induce apoptosis may be observed by mitosensor ApoAlert confocal microscopy using a MITOSENSOR™ APOLERT™ Mitochondrial Membrane Sensor kit (Clontech Laboratories, Inc., Palo Alto, Calif., U.S.A.), by measuring caspase-8, caspase-9 and caspase-3 activity using the method described in Zou et al. (*J. Biol. Chem.* 274: 11549-11556 (1999)), and by detecting apoptosis-induced nuclear DNA fragmentation using, for example, the APOLERT™ DNA fragmentation kit (Clontech Laboratories, Inc., Palo Alto, Calif., U.S.A.).

In another specific embodiment, the peptide of the invention induces cellular growth arrest in a mammalian cancer cell, more specifically a J774 cell. Cellular growth arrest can be determined by measuring the extent of inhibition of cell cycle progression, such as by the method found in Yamada et al. (*PNAS* 101:4770-4775 (2004)). In another specific embodiment, the cupredoxin or cytochrome $c_{551}$, or variant, derivative or structural equivalent thereof inhibits cell cycle progression in a mammalian cancer cell, more specifically a J774 cell.

Cupredoxins

These small blue copper proteins (cupredoxins) are electron transfer proteins (10-20 kDa) that participate in bacterial electron transfer chains or are of unknown function. The copper ion is solely bound by the protein matrix. A special distorted trigonal planar arrangement to two histidine and one cysteine ligands around the copper gives rise to very peculiar electronic properties of the metal site and an intense blue color. A number of cupredoxins have been crystallographically characterized at medium to high resolution.

The cupredoxins in general have a low sequence homology but high structural homology. (Gough & Clothia, *Structure* 12:917-925 (2004); De Rienzo et al., *Protein Science* 9:1439-1454 (2000)). For example, the amino acid sequence of azurin is 31% identical to that of auracyanin B, 16.3% to that of rusticyanin, 20.3% to that of plastocyanin, and 17.3% to that of pseudoazurin. See, Table 1. However, the structural similarity of these proteins is more pronounced. The VAST p value for the comparison of the structure of azurin to auracyanin B is $10^{-7.4}$, azurin to rusticyanin is $10^{-5}$, azurin to plastocyanin is $10^{-5.6}$, and azurin to psuedoazurin is $10^{-4.1}$.

All of the cupredoxins possess an eight-stranded Greek key beta-barrel or beta-sandwich fold and have a highly conserved site architecture. (De Rienzo et al., *Protein Science* 9:1439-1454 (2000)) A prominent hydrophobic patch, due to the presence of many long chain aliphatic residues such as methionines and leucines, is present around the copper site in azurins, amicyanins, cyanobacterial plastocyanins, cucumber basic protein and to a lesser extent, pseudoazurin and eukaryotic plastocyanins. Id. Hydrophobic patches are also found to a lesser extent in stellacyanin and rusticyanin copper sites, but have different features. Id.

TABLE 1

Sequence and structure alignment of azurin (1JZG) from *P. aeruginosa* to other proteins using VAST algorithm.

| PDB | Alignment length[1] | % aa identity | P-value[2] | Score[3] | RMSD[4] | Description |
|---|---|---|---|---|---|---|
| 1AOZ A 2 | 82 | 18.3 | 10e−7 | 12.2 | 1.9 | Ascorbate oxidase |
| 1QHQ_A | 113 | 31 | 10e−7.4 | 12.1 | 1.9 | AuracyaninB |
| 1V54 B 1 | 79 | 20.3 | 10e−6.0 | 11.2 | 2.1 | Cytocrome c oxidase |
| 1GY2 A | 92 | 16.3 | 10e−5.0 | 11.1 | 1.8 | Rusticyanin |
| 3MSP A | 74 | 8.1 | 10e−6.7 | 10.9 | 2.5 | Motile Major Sperm Protein[5] |
| 1IUZ | 74 | 20.3 | 10e−5.6 | 10.3 | 2.3 | Plastocyanin |
| 1KGY E | 90 | 5.6 | 10e−4.6 | 10.1 | 3.4 | Ephrinb2 |
| 1PMY | 75 | 17.3 | 10e−4.1 | 9.8 | 2.3 | Pseudoazurin |

[1]Aligned Length: The number of equivalent pairs of C-alpha atoms superimposed between the two structures, i.e. how many residues have been used to calculate the 3D superposition.
[2]P-VAL: The VAST p value is a measure of the significance of the comparison, expressed as a probability. For example, if the p value is 0.001, then the odds are 1000 to 1 against seeing a match of this quality by pure chance. The p value from VAST is adjusted for the effects of multiple comparisons using the assumption that there are 500 independent and unrelated types of domains in the MMDB database. The p value shown thus corresponds to the p value for the pairwise comparison of each domain pair, divided by 500.
[3]Score: The VAST structure-similarity score. This number is related to the number of secondary structure elements superimposed and the quality of that superposition. Higher VAST scores correlate with higher similarity.
[4]RMSD: The root mean square superposition residual in Angstroms. This number is calculated after optimal superposition of two structures, as the square root of the mean square distances between equivalent C-alpha atoms. Note that the RMSD value scales with the extent of the structural alignments and that this size must be taken into consideration when using RMSD as a descriptor of overall structural similarity.
[5]*C. elegans* major sperm protein proved to be an ephrin antagonist in oocyte maturation (Kuwabara, 2003 "The multifaceted *C. elegans* major sperm protein: an ephrin signalling antagonist in oocyte maturation" Genes and Development, 17: 155-161.

Azurin

The azurins are copper containing proteins of 128 amino acid residues which belong to the family of cupredoxins involved in electron transfer in certain bacteria. The azurins include those from *P. aeruginosa* (PA) (SEQ ID NO: 1), *A. xylosoxidans*, and *A. denitrificans*. (Murphy et al., J. Mol. Biol. 315:859-871 (2002)) The amino acid sequence identity between the azurins varies between 60-90%, these proteins showed a strong structural homology. All azurins have a characteristic β-sandwich with Greek key motif and the single copper atom is always placed at the same region of the protein. In addition, azurins possess an essentially neutral hydrophobic patch surrounding the copper site. Id.

Plastocyanins

The plastocyanins are soluble proteins of cyanobacteria, algae and plants that contain one molecule of copper per molecule and are blue in their oxidized form. They occur in the chloroplast, where they function as electron carriers. Since the determination of the structure of poplar plastocyanin in 1978, the structure of algal (*Scenedesmus, Enteromorpha, Chlamydomonas*) and plant (French bean) plastocyanins has been determined either by crystallographic or NMR methods, and the poplar structure has been refined to 1.33 Å resolution. SEQ ID NO: 3 shows the amino acid sequence of plastocyanin from *Phormidium laminosum*, a thermophilic cyanobacterium.

Despite the sequence divergence among plastocyanins of algae and vascular plants (e.g., 62% sequence identity between the *Chlamydomonas* and poplar proteins), the three-dimensional structures are conserved (e.g., 0.76 Å rms deviation in the C alpha positions between the *Chlamydomonas* and Poplar proteins). Structural features include a distorted tetrahedral copper binding site at one end of an eight-stranded antiparallel beta-barrel, a pronounced negative patch, and a flat hydrophobic surface. The copper site is optimized for its electron transfer function, and the negative and hydrophobic patches are proposed to be involved in recognition of physiological reaction partners. Chemical modification, cross-linking, and site-directed mutagenesis experiments have confirmed the importance of the negative and hydrophobic patches in binding interactions with cytochrome f, and validated the model of two functionally significant electron transfer paths involving plastocyanin. One putative electron transfer path is relatively short (approximately 4 Å) and involves the solvent-exposed copper ligand His-87 in the hydrophobic patch, while the other is more lengthy (approximately 12-15 Å) and involves the nearly conserved residue Tyr-83 in the negative patch, Redinbo et al., J. Bioenerg. Biomembr. 26:49-66 (1994).

Rusticyanins

Rusticyanins are blue-copper containing single-chain polypeptides obtained from a *Thiobacillus* (now called *Acidithiobacillus*). The X-ray crystal structure of the oxidized form of the extremely stable and highly oxidizing cupredoxin rusticyanin from *Thiobacillus ferrooxidans* (SEQ ID NO: 4) has been determined by multiwavelength anomalous diffraction and refined to 1.9 Å resolution. The rusticyanins are composed of a core beta-sandwich fold composed of a six- and a seven-stranded b-sheet. Like other cupredoxins, the copper ion is coordinated by a cluster of four conserved residues (His 85, Cys138, His143, Met148) arranged in a distorted tetrahedron. Walter, R. L. et al., J. Mol. Biol. 263:730-51 (1996).

Pseudoazurins

The pseudoazurins are a family of blue-copper containing single-chain polypeptide. The amino acid sequence of pseudoazurin obtained from *Achromobacter cycloclastes* is shown in SEQ ID NO: 5. The X-ray structure analysis of pseudoazurin shows that it has a similar structure to the azurins although there is low sequence homology between these proteins. Two main differences exist between the overall structure of the pseudoazurins and azurins. There is a carboxy terminus extension in the pseudoazurins, relative to the azurins, consisting of two alpha-helices. In the midpeptide region azurins contain an extended loop, shortened in the pseudoazurins, which forms a flap containing a short α-helix. The only major differences at the copper atom site are the conformation of the MET side-chain and the Met-S copper bond length, which is significantly shorter in pseudoazurin than in azurin.

Phytocyanins

The proteins identifiable as phytocyanins include, but are not limited to, cucumber basic protein, stellacyanin, mavicyanin, umecyanin, a cucumber peeling cupredoxin, a putative blue copper protein in pea pods, and a blue copper protein from *Arabidopsis thaliana*. In all except cucumber basic protein and the pea-pod protein, the axial methionine ligand normally found at blue copper sites is replaced by glutamine.

Auracyanin

Three small blue copper proteins designated auracyanin A, auracyanin B-1, and auracyanin B-2 have been isolated from the thermophilic green gliding photosynthetic bacterium *Chloroflexus aurantiacus*. The two B forms are glycoproteins and have almost identical properties to each other, but are distinct from the A form. The sodium dodecyl sulfate-polyacrylamide gel electrophoresis demonstrates apparent monomer molecular masses as 14 (A), 18 (B-2), and 22 (B-1) kDa.

The amino acid sequence of auracyanin A has been determined and showed auracyanin A to be a polypeptide of 139 residues. (Van Dreissche et al; *Protein Science* 8:947-957 (1999).) His58, Cys123, His128, and Met132 are spaced in a way to be expected if they are the evolutionary conserved metal ligands as in the known small copper proteins plastocyanin and azurin. Secondary structure prediction also indicates that auracyanin has a general beta-barrel structure similar to that of azurin from *Pseudomonas aeruginosa* and plastocyanin from poplar leaves. However, auracyanin appears to have sequence characteristics of both small copper protein sequence classes. The overall similarity with a consensus sequence of azurin is roughly the same as that with a consensus sequence of plastocyanin, namely 30.5%. The N-terminal sequence region 1-18 of auracyanin is remarkably rich in glycine and hydroxy amino acids. Id See exemplary amino acid sequence SEQ ID NO: 15 for chain A of auracyanin from *Chloroflexus aurantiacus* (NCBI Protein Data Bank Accession No. AAM12874).

The auracyanin B molecule has a standard cupredoxin fold. The crystal structure of auracyanin B from *Chloroflexus aurantiacus* has been studied. (Bond et al., *J. Mol. Biol.* 306:47-67 (2001).) With the exception of an additional N-terminal strand, the molecule is very similar to that of the bacterial cupredoxin, azurin. As in other cupredoxins, one of the Cu ligands lies on strand 4 of the polypeptide, and the other three lie along a large loop between strands 7 and 8. The Cu site geometry is discussed with reference to the amino acid spacing between the latter three ligands. The crystallographically characterized Cu-binding domain of auracyanin B is probably tethered to the periplasmic side of the cytoplasmic membrane by an N-terminal tail that exhibits significant sequence identity with known tethers in several other membrane-associated electron-transfer proteins. The amino acid sequences of the B forms are presented in McManus et al. (*J Biol Chem.* 267:6531-6540 (1992).). See exemplary amino acid sequence SEQ ID NO: 16 for chain B of auracyanin from *Chloroflexus aurantiacus* (NCBI Protein Data Bank Accession No. 1QHQA).

Stellacyanin

Stellacyanins are a subclass of phytocyanins, a ubiquitous family of plant cupredoxins. An exemplary sequence of a stellacyanin is included herein as SEQ ID NO: 14. The crystal structure of umecyanin, a stellacyanin from horse-radish root (Koch et al., *J. Am. Chem. Soc.* 127:158-166 (2005)) and cucumber stellacyanin (Hart et al., *Protein Science* 5:2175-2183 (1996)) is also known. The protein has an overall fold similar to the other phytocyanins. The ephrin B2 protein ectodomain tertiary structure bears a significant similarity to stellacyanin. (Toth et al., *Developmental Cell* 1:83-92 (2001).) An exemplary amino acid sequence of a stellacyanin is found in the National Center for Biotechnology Information Protein Data Bank as Accession No. 1JER, SEQ ID NO: 14.

Cucumber Basic Protein

An exemplary amino acid sequence from a cucumber basic protein is included herein as SEQ ID NO: 17. The crystal structure of the cucumber basic protein (CBP), a type 1 blue copper protein, has been refined at 1.8 Å resolution. The molecule resembles other blue copper proteins in having a Greek key beta-barrel structure, except that the barrel is open on one side and is better described as a "beta-sandwich" or "beta-taco". (Guss et al., *J. Mol. Biol.* 262: 686-705 (1996).) The ephrinB2 protein ectodomian tertiary structure bears a high similarity (rms deviation 1.5 Å for the 50α carbons) to the cucumber basic protein. (Toth et al., *Developmental Cell* 1:83-92 (2001).)

The Cu atom has the normal blue copper NNSS' co-ordination with bond lengths Cu—N(His39)=1.93 A, Cu—S (Cys79)=2.16 A, Cu—N(His84)=1.95 A, Cu—S(Met89)=2.61 A. A disulphide link, (Cys52)-S—S-(Cys85), appears to play an important role in stabilizing the molecular structure. The polypeptide fold is typical of a sub-family of blue copper proteins (phytocyanins) as well as a non-metalloprotein, ragweed allergen Ra3, with which CBP has a high degree of sequence identity. The proteins currently identifiable as phytocyanins are CBP, stellacyanin, mavicyanin, umecyanin, a cucumber peeling cupredoxin, a putative blue copper protein in pea pods, and a blue copper protein from *Arabidopsis thaliana*. In all except CBP and the pea-pod protein, the axial methionine ligand normally found at blue copper sites is replaced by glutamine. An exemplary sequence for cucumber basic protein is found in NCBI Protein Data Bank Accession No. 2CBP, SEQ ID NO: 17.

Methods of Use

The invention provides a method to treat a patient infected with viral or bacterial infection, and specifically HIV-1 infection, comprising administering to the patient at least one polypeptide that is a cupredoxin or cytochrome $c_{551}$, or variant, derivative or structural equivalent thereof, as described above. It is also contemplated that the same method will be effective to treat patients with other viral or bacterial infections, such as, but not limited to, Herpes simplex virus (HSV), Ebola virus, cytomeglovirus (CMV), parainfluenza viruses types A, B and C, etc., hepatitis A, B, C, G, the delta hepatitis virus (HDV), mumps viruses, measles viruses, respiratory syncytial viruses, bunyviruses, arena viruses, the orthomyxo-like insect virus called Dhori, polioviruses, rubella virus, dengue virus; SIV and *Mycobacterium tuberculosis*.

It has also been learned that cupredoxins and cytochrome c are also effective against malarial infections, as disclosed in a co-filed application. Further, co-infections with HIV and malaria are very common in many areas of the world, and in particular sub-Saharan Africa. In some embodiments, the patient suffering from infection by HIV is also suffering from infection by a malaria parasite. In some embodiments, the method of treatment of the invention also comprises administering anti-malarial drugs. In some embodiments, the anti-malarial drugs are co-administered.

The methods of the invention include contacting mammalian cells with a composition comprising cupredoxin or cytochrome $c_{551}$, or variant, derivative or structural equivalent thereof. In some embodiments, the mammalian cells are infected with a virus or bacteria, such as HIV-1. In other embodiments, the mammalian cells will be exposed to a virus or bacteria, such as HIV-1.

The composition comprising cupredoxin or cytochrome $c_{551}$, or variant, derivative or structural equivalent thereof can be administered to the patient by many routes and in many regimens that will be well known to those in the art. In specific embodiments, the cupredoxin or cytochrome $c_{551}$, or variant, derivative or structural equivalent thereof is administered intravenously, intramuscularly or subcutaneously.

In one embodiment, the methods may comprise co-administering to a patient one unit dose of a composition comprising a cupredoxin or cytochrome $c_{551}$, or a variant, derivative or structural equivalent of cupredoxin or cytochrome $c_{551}$, and one unit dose of a composition comprising another anti-viral or anti-bacterial, and specifically anti-HIV drug and/or an anti-malarial drug, in either order, administered at about the same time, or within about a given time following the administration of the other, for example, about one minute to about 60 minutes following the administration of the other drug, or about 1 hour to about 12 hours following the administration of the other drug.

In addition, the present invention includes methods useful for studying viral and bacterial infection. In some embodiments, the method comprises contacting mammalian cells infected with a virus or bacteria with a cupredoxin or cytochrome $c_{551}$, or variant, derivative or structural equivalent thereof, and measuring the growth of infection. In other embodiments, the method comprises contacting mammalian cells with a cupredoxin or cytochrome $c_{551}$, or variant, derivative or structural equivalent thereof, contacting the mammalian cells with a virus or bacteria, and measuring the growth of infection in the cells. In some embodiments, the bacteria or virus is HIV, Herpes simplex virus (HSV), Ebola virus, cytomeglovirus (CMV), parainfluenza viruses types A, B and C, etc., hepatitis A, B, C, G, the delta hepatitis virus (HDV), mumps viruses, measles viruses, respiratory syncytial viruses, bunyviruses, arena viruses, the orthomyxo-like insect virus called Dhori, polioviruses, rubella virus, dengue virus; SIV and *Mycobacterium tuberculosis*. In a specific embodiment, the virus is HIV-1, and particularly strains Bal, 2167, or RW/92/008/RE1. In other embodiments, the mammalian cells are human. In other embodiments, the cells are blood lymphocytes or peripheral blood mononuclear cells. In various embodiments, the cells are contacted in the animal (in vivo), or outside the animal (in vitro). In some embodiments, the cells are contacted in vitro and them introduced into an animal.

Pharmaceutical Compositions Comprising Cupredoxin or Cytochrome $C_{551}$, or Variant, Derivative or Structural Equivalent Thereof Pharmaceutical compositions comprising cupredoxin or cytochrome $c_{551}$, or variant, derivative or structural equivalents thereof, can be manufactured in any conventional manner, e.g. by conventional mixing, dissolving, granulating, dragee-making, emulsifying, encapsulating, entrapping, or lyophilizing processes. The substantially pure cupredoxin and/or cytochrome $c_{551}$, and variants, derivatives and structural equivalents thereof can be readily combined with a pharmaceutically acceptable carrier well-known in the art. Such carriers enable the preparation to be formulated as a tablet, pill, dragee, capsule, liquid, gel, syrup, slurry, suspension, and the like. Suitable carriers or excipients can also include, for example, fillers and cellulose preparations. Other excipients can include, for example, flavoring agents, coloring agents, detackifiers, thickeners, and other acceptable additives, adjuvants, or binders. In some embodiments, the pharmaceutical preparation is substantially free of preservatives. In other embodiments, the pharmaceutical preparation may contain at least one preservative. General methodology on pharmaceutical dosage forms is found in Ansel et al., *Pharmaceutical Dosage Forms and Drug Delivery Systems* (Lippencott Williams & Wilkins, Baltimore Md. (1999)).

The composition comprising a cupredoxin or cytochrome $c_{551}$, or variant, derivative or structural equivalent thereof used in the invention may be administered in a variety of ways, including by injection (e.g., intradermal, subcutaneous, intramuscular, intraperitoneal and the like), by inhalation, by topical administration, by suppository, by using a transdermal patch or by mouth. General information on drug delivery systems can be found in Ansel et al., Id. In some embodiments, the composition comprising a cupredoxin or cytochrome $c_{551}$, or variant, derivative or structural equivalent thereof can be formulated and used directly as injectables, for subcutaneous and intravenous injection, among others. The injectable formulation, in particular, can advantageously be used to treat patients that are at risk of, likely to have or have a viral or bacterial infection, and specifically an HIV-infection. The composition comprising a cupredoxin or cytochrome $c_{551}$, or variant, derivative or structural equivalent thereof can also be taken orally after mixing with protective agents such as polypropylene glycols or similar coating agents.

When administration is by injection, the cupredoxin or cytochrome $c_{551}$, or variant, derivative or structural equivalent thereof may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the cupredoxin or cytochrome $c_{551}$, or variant, derivative or structural equivalent thereof may be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide.

When administration is by intravenous fluids, the intravenous fluids for use administering the cupredoxin or cytochrome $c_{551}$, or variant, derivative or structural equivalent thereof may be composed of crystalloids or colloids. Crystalloids as used herein are aqueous solutions of mineral salts or other water-soluble molecules. Colloids as used herein contain larger insoluble molecules, such as gelatin. Intravenous fluids may be sterile.

Crystalloid fluids that may be used for intravenous administration include but are not limited to, normal saline (a solution of sodium chloride at 0.9% concentration), Ringer's lactate or Ringer's solution, and a solution of 5% dextrose in water sometimes called D5W, as described in Table 2.

TABLE 2

Composition of Common Crystalloid Solutions

| Solution | Other Name | [Na$^+$] | [Cl$^-$] | [Glucose] |
|---|---|---|---|---|
| D5W | 5% Dextrose | 0 | 0 | 252 |
| ⅔ & ⅓ | 3.3% Dextrose/ 0.3% saline | 51 | 51 | 168 |
| Half-normal saline | 0.45% NaCl | 77 | 77 | 0 |

TABLE 2-continued

Composition of Common Crystalloid Solutions

| Solution | Other Name | [Na$^+$] | [Cl$^-$] | [Glucose] |
|---|---|---|---|---|
| Normal saline | 0.9% NaCl | 154 | 154 | 0 |
| Ringer's lactate* | Ringer's solution | 130 | 109 | 0 |

*Ringer's lactate also has 28 mmol/L lactate, 4 mmol/L K$^+$ and 3 mmol/L Ca$^{2+}$.

When administration is by inhalation, the cupredoxin or cytochrome $c_{551}$, or variant, derivative or structural equivalent thereof may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the proteins and a suitable powder base such as lactose or starch.

When administration is by topical administration, the cupredoxin or cytochrome $c_{551}$, or variant, derivative or structural equivalent thereof may be formulated as solutions, gels, ointments, creams, jellies, suspensions, and the like, as are well known in the art. In some embodiments, administration is by means of a transdermal patch. When administration is by suppository (e.g., rectal or vaginal), cupredoxin and/or cytochrome c and variants and derivatives thereof compositions may also be formulated in compositions containing conventional suppository bases.

When administration is oral, a cupredoxin or cytochrome $c_{551}$, or variant, derivative or structural equivalent thereof can be readily formulated by combining the cupredoxin or cytochrome $c_{551}$, or variant, derivative or structural equivalent thereof with pharmaceutically acceptable carriers well known in the art. A solid carrier, such as mannitol, lactose, magnesium stearate, and the like may be employed; such carriers enable the cupredoxin and/or cytochrome c and variants and derivatives thereof to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Other convenient carriers, as well-known in the art, also include multivalent carriers, such as bacterial capsular polysaccharide, a dextran or a genetically engineered vector. In addition, sustained-release formulations that include a cupredoxin or cytochrome $c_{551}$, or variant, derivative or structural equivalent thereof allow for the release of cupredoxin or cytochrome $c_{551}$, or variant, derivative or structural equivalent thereof over extended periods of time, such that without the sustained release formulation, the cupredoxin or cytochrome $c_{551}$, or variant, derivative or structural equivalent thereof would be cleared from a subject's system, and/or degraded by, for example, proteases and simple hydrolysis before eliciting or enhancing a therapeutic effect.

The half-life in the bloodstream of the compositions of the invention can be extended or optimized by several methods well known to those in the art, including but not limited to, circularized peptides (Monk et al., BioDrugs 19(4):261-78, (2005); DeFreest et al., J. Pept. Res. 63(5):409-19 (2004)), D,L-peptides (diastereomer), (Futaki et al., J. Biol. Chem. February 23; 276(8):5836-40 (2001); Papo et al., Cancer Res. 64(16):5779-86 (2004); Miller et al., Biochem. Pharmacol. 36(1):169-76, (1987)); peptides containing unusual amino acids (Lee et al., J. Pept. Res. 63(2):69-84 (2004)), N- and C-terminal modifications (Labrie et al., Clin. Invest. Med. 13(5):275-8, (1990)), and hydrocarbon stapling (Schafmeister et al., J. Am. Chem. Soc. 122:5891-5892 (2000); Walenski et al., Science 305:1466-1470 (2004)). Of particular interest are d-isomerization (substitution) and modification of peptide stability via D-substitution or L-amino acid substitution.

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration.

Administration of Cupredoxin or Cytochrome $C_{551}$, or Variant, Derivative or Structural Equivalent Thereof The cupredoxin or cytochrome $c_{551}$, or variant, derivative or structural equivalent thereof can be administered formulated as pharmaceutical compositions and administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary) administration. The pharmaceutical formulations thereof can be administered in any amount effective to achieve its intended purpose. More specifically, the composition is administered in a therapeutically effective amount. In specific embodiments, the therapeutically effective amount is generally from about 0.01-20 mg/day/kg of body weight.

The compounds comprising cupredoxin or cytochrome $c_{551}$, or variant, derivative or structural equivalent thereof are useful for the treatment and/or prophylaxis of HIV infection or other viral or bacterial infections, alone or in combination with other active agents. The appropriate dosage will, of course, vary depending upon, for example, the compound of cupredoxin or cytochrome $c_{551}$, or variant, derivative or structural equivalent thereof employed, the host, the mode of administration and the nature and severity of the conditions being treated. However, in general, satisfactory results in humans are indicated to be obtained at daily dosages from about 0.01-20 mg/kg of body weight. An indicated daily dosage in humans is in the range from about 0.7 mg to about 1400 mg of a compound of cupredoxin or cytochrome $c_{551}$, or variant, derivative or structural equivalent thereof conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days. Alternatively, dosing can be continuous using patches, i.v. administration and the like.

The method of introducing cupredoxin or cytochrome $c_{551}$, or variant, derivative or structural equivalent thereof to patients is, in some embodiments, the same as currently used to introduce anti-HIV drugs, such as the protease-inhibitor-containing cocktails. Such methods are well-known in the art. In a specific embodiment, the cupredoxin or cytochrome $c_{551}$, or variant, derivative or structural equivalent thereof are part of an cocktail or co-dosing containing or with other anti-HIV therapeutics. Other anti-HIV drugs include, but are not limited to, reverse transcriptase inhibitors: AZT (zidovudine [Retrovir]), ddC (zalcitabine [Hivid], dideoxyinosine), d4T (stavudine [Zerit]), and 3TC (lamivudine [Epivir]), nonnucleoside reverse transcriptase inhibitors (NNRTIS): delavirdine (Rescriptor) and nevirapine (Viramune), protease inhibitors: ritonavir (Norvir), a lopinavir and ritonavir combination (Kaletra), saquinavir (Invirase), indinavir sulphate (Crixivan), amprenavir (Agenerase), and nelfinavir (Viracept). Presently, a combination of several drugs called highly active antiretroviral therapy (HAART) is used to treat people with HIV.

The method of introducing cupredoxin or cytochrome, or variant, derivative or structural equivalent thereof to patients is, in some embodiments, through the co-administration of cupredoxin or cytochrome, or variant, derivative or structural equivalent thereof with drugs used for malaria therapy. Such methods are well-known in the art. In a specific embodiment, the cupredoxin and/or cytochrome c are part of an cocktail or co-dosing containing or with malaria therapeutics. Malaria therapeutics of interest include, but are not limited to, proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, proguanil, chloroquine, mefloquine, pyrimethamine-sulfadoxine, pyrimethamine-dapsone, halofantrine, quinine, proguanil, chloroquine, mefloquine, 1,16-hexadecamethylenebis(N-methylpyrrolidinium)dibromide, and combinations thereof.

The exact formulation, route of administration, and dosage is determined by the attending physician in view of the patient's condition. Dosage amount and interval can be adjusted individually to provide plasma levels of the active cupredoxin or cytochrome $c_{551}$, or variant, derivative or structural equivalent thereof which are sufficient to maintain therapeutic effect. Generally, the desired cupredoxin or cytochrome $c_{551}$, or variant, derivative or structural equivalent thereof is administered in an admixture with a pharmaceutical carrier selected with regard to the intended route of administration and standard pharmaceutical practice.

In one aspect, the cupredoxin or cytochrome $c_{551}$, or variant, derivative or structural equivalent thereof is delivered as DNA such that the polypeptide is generated in situ. In one embodiment, the DNA is "naked," as described, for example, in Ulmer et al., (Science 259:1745-1749 (1993)) and reviewed by Cohen (Science 259:1691-1692 (1993)). The uptake of naked DNA may be increased by coating the DNA onto a carrier, e.g., biodegradable beads, which are then efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: Cloning vectors are replicating plasmid or phage with regions that are essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of a cupredoxin. In expression vectors, the introduced DNA is operably-linked to elements such as promoters that signal to the host cell to highly transcribe the inserted DNA. Some promoters are exceptionally useful, such as inducible promoters that control gene transcription in response to specific factors. Operably-linking a cupredoxin and/or cytochrome c and variants and derivatives thereof polynucleotide to an inducible promoter can control the expression of the cupredoxin and/or cytochrome c and variants and derivatives thereof in response to specific factors. Examples of classic inducible promoters include those that are responsive to α-interferon, heat shock, heavy metal ions, and steroids such as glucocorticoids (Kaufman, Methods Enzymol. 185:487-511 (1990)) and tetracycline. Other desirable inducible promoters include those that are not endogenous to the cells in which the construct is being introduced, but, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. In general, vectors comprise signal sequences, origins of replication, marker genes, polylinker sites, enhancer elements, promoters, and transcription termination sequences.

Kits Comprising Cupredoxin or Cytochrome $C_{551}$, or Variant, Derivative or Structural Equivalent Thereof In one aspect, the invention provides kits containing one or more of the following in a package or container: (1) a biologically active composition comprising at least one cupredoxin or cytochrome $c_{551}$, or variant, derivative or structural equivalent thereof; (2) an anti-viral or anti-bacterial drug, specifically an anti-HIV drug, including, but not limited to, reverse transcriptase inhibitors: AZT (zidovudine [Retrovir]), ddC (zalcitabine [Hivid], dideoxyinosine), d4T (stavudine [Zerit]), and 3TC (lamivudine [Epivir]), nonnucleoside reverse transcriptase inhibitors (NNRTIS): delavirdine (Rescriptor) and nevirapine (Viramune), protease inhibitors: ritonavir (Norvir), a lopinavir and ritonavir combination (Kaletra), saquinavir (Invirase), indinavir sulphate (Crixivan), amprenavir (Agenerase), and nelfinavir (Viracept); (3) a pharmaceutically acceptable excipient; (4) a vehicle for administration, such as a syringe; (5) instructions for administration. Embodiments in which two or more of components (1)-(5) are found in the same packaging or container are also contemplated.

In some embodiments, the kit also comprises an anti-malarial therapeutic. Anti-malarial therapeutics of interest include, but are not limited to, proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, proguanil, chloroquine, mefloquine, pyrimethamine-sulfadoxine, pyrimethamine-dapsone, halofantrine, quinine, proguanil, chloroquine, mefloquine, 1,16-hexadecamethylenebis(N-methylpyrrolidinium)dibromide.

When a kit is supplied, the different components of the composition may be packaged in separate containers and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampules may contain lyophilized cupredoxin and/or cytochrome c and variants and derivatives thereof, or buffers that have been packaged under a neutral, non-reacting gas, such as nitrogen. Ampules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device etc. Detailed instructions may not be physically associated with the kit; instead, a user may be directed to an internet web site specified by the manufacturer or distributor of the kit, or supplied as electronic mail.

Modification of Cupredoxin and/or Cytochrome C and Variants and Derivatives Thereof Cupredoxin or cytochrome $c_{551}$, or variant, derivative or structural equivalents thereof may be chemically modified or genetically altered to produce variants and derivatives as explained above. Such variants and derivatives may be synthesized by standard techniques.

In addition to naturally-occurring allelic variants of cupredoxin and cytochrome $c_{551}$, changes can be introduced by mutation into cupredoxin or cytochrome $c_{551}$ coding sequence that incur alterations in the amino acid sequences of the encoded cupredoxin or cytochrome $c_{551}$ that do not significantly alter the ability of cupredoxin or cytochrome c to inhibit the growth of a viral or bacterial infection, and specifically an HIV infection in mammalian cells. A "non-essential" amino acid residue is a residue that can be altered from the wild-type sequences of the cupredoxin without altering biological activity, whereas an "essential" amino acid residue is required for such biological activity. For example, amino acid residues that are conserved among the cupredoxins are predicted to be particularly non-amenable to alteration, and thus "essential."

Amino acids for which conservative substitutions that do not change the activity of the polypeptide can be made are well known in the art. Useful conservative substitutions are shown in Table 3, "Preferred substitutions." Conservative substitutions whereby an amino acid of one class is replaced with another amino acid of the same type fall within the scope of the invention so long as the substitution does not materially alter the biological activity of the compound.

TABLE 3

Preferred substitutions

| Original residue | Exemplary substitutions | Preferred substitutions |
| --- | --- | --- |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge, (3) hydrophobicity, or (4) the bulk of the side chain of the target site can modify the cytotoxic factor function. Residues are divided into groups based on common side-chain properties as denoted in Table 4. Non-conservative substitutions entail exchanging a member of one of these classes for another class. Substitutions may be introduced into conservative substitution sites or more specifically into non-conserved sites.

TABLE 4

Amino acid classes

| Class | Amino acids |
| --- | --- |
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, Biochem J. 237:1-7 (1986); Zoller and Smith, Methods Enzymol. 154:329-350 (1987)), cassette mutagenesis, restriction selection mutagenesis (Wells et al., Gene 34:315-323 (1985)) or other known techniques can be performed on the cloned DNA to produce the cupredoxin or cytochrome $c_{551}$ variant DNA.

Known mutations of cupredoxins and cytochrome $c_{551}$ can also be used to create variant cupredoxin and cytochrome $c_{551}$ to be used in the methods of the invention. For example, the C112D and M44KM64E mutants of azurin are known to have cytotoxic and growth arresting activity that is different from the native azurin, and such altered activity can be useful in the treatment methods of the present invention. One embodiment of the methods of the invention utilize cupredoxin and/or cytochrome $c_{551}$ and variants and derivatives thereof retaining the ability inhibit the growth of an viral or bacterial infection, and specifically HIV infection in mammalian cells. In another embodiment, the methods of the present invention utilize cupredoxin variants such as the M44KM64E mutant, having the ability to cause cellular growth arrest.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof, and, therefore, only such limitations should be imposed as are indicated by the appended embodiments.

EXAMPLES

Example 1: In Vivo Inhibition of HIV Infection of Lymphocytes by Azurin Mutant and Cytochrome $C_{551}$ The M44KM64E mutant of azurin was mixed with cytochrome $c_{551}$ on a 1:1 basis (1 µM azurin: 1 µM cytochrome $c_{551}$). HIV-infected human blood lymphocytes were incubated with the mixed azurin/cytochrome $c_{551}$ proteins at concentrations of 0, 500 to 1000 µg/ml protein for 7 days. The HIV p24 levels were then measured in the infected lymphocytes. p24 levels are known to be colinear with HIV virus levels in infected blood. Measuring the change in p24 concentrations in blood will indicate the change of HIV virus titer in the blood. Controls with non-infected human blood lymphocytes were also run in a parallel manner. After the 7 day incubation, the HIV p24 levels in the infected lymphocytes were reduced by 25% to 90% as compared to the control infected lymphocytes with 0 µg/ml azurin and cytochrome $c_{551}$. In the non-infected control cells, after 7 days of incubation with the protein mixture, neither cell death nor cytotoxicity was found.

Example 2: Azurin Exhibits Structural Similarity with ICAM-1 from HIV-1

Previous studies (Gough & Chothia, Structure 12:917-925 (2004); Stevens et al., J. Mol. Recognit. 18:150-157 (2005)) have shown that cupredoxins show structural similarity to the variable domains of the immunoglobulin superfamily members. The DALI algorithm (Holm & Park, Bioinformatics 16:566-567 (2000)) was used to search the 3D databases for structural homologs of azurin (1JZG) from *P. aeruginosa*. See, Table 5. Azurin exhibits structural similarity to not only the fab fragment of the monoclonal antibody in complexation with PfMSP1-19, but also to ICAM-1 (Table 5) involved in cerebral malaria (Smith et al., Proc. Natl. Acad. Sci. USA 97:1766-1771 (2000); Franke-Fayard et al., Proc. Natl. Acad. Sci. USA 102:11468-11473 (2005))

ICAM-1 is not only implicated as a receptor on the endothelial cells in the microvasculture of the brain and other tissues for sequestering *P. falciparum*-infected erythrocytes, but is also found in HIV-1 particles during their passage through the host cells and is known to enhance HIV-1 infectivity by enhancing cytosolic delivery of the viral materials. (Fortin et al., J. Virol. 71:3588-3596 (1997); Tardif & Tremblay, J. Virol. 77:12299-12309 (2003)) ICAM-1 is known also to be subverted as receptors for major groups of rhinoviruses and coxsackie viruses. (Bella & Rossmann, J. Struct. Biol. 128:69-74 (1999))

Azurin demonstrates structural similarity to CD4 (Table 5), the primary host cell surface receptor for HIV-1. (Maddon et al., Cell 47:333-348 (1986)) This example shows that cupredoxins including azurin demonstrate structural similarities in having two anti-parallel β sheets packed face to face and linked by a disulfide bridge to the variable domains of the immunoglobulin superfamily members as well as extracellular domains of the intercellular adhesion molecules (ICAM) and their ligands.

TABLE 5

Structural similarity of *P. aeruginosa* azurin with various pathogenesis-related proteins

| | | | Azurin (1jzg) | | |
| --- | --- | --- | --- | --- | --- |
| PDB | Annotation | Reference | DALI z score[1] | RMSD to Azurin[2] | Alignment length |
| 1VCA B1 | Human Vascular Cell Adhesion | 17 | 3.5 | 3.2 | 80 |
| 1CDH | CD4 (D1D2 Fragment) Type I Crystal Form | 18 | 3.4 | 2.8 | 73 |
| 1ZXQ1 | Crystal Structure of ICAM-2 | 19 | 3.3 | 2.9 | 80 |
| 1IAM1 | Structure of the Two Amino-Terminal Adhesion Molecule-1, ICAM-1 | 20 | 3.3 | 3.1 | 74 |
| 1OB1 A1 | Crystal Structure of a Fab Complex with *Plasmodium falciparum* MSP1-19 | 21 | 2.9 | 3.7 | 84 |

Structural alignment of azurin were made using DALI (Holm & Park, Bioinformatics 16:566-567 (2000)). Structure pairs with DALI z scores <2 are considered dissimilar. RMSD-Root-mean-square deviation of backbone residues in angstroms between the aligned parts of the pair of structure.

Example 3: Effect of Azurin, H.8-Azurin and Laz on HIV-1 Entry and Viral Growth

The effect of various concentrations of azurin, H.8-azurin and Laz on the growth of three subtypes of HIV-1 in peripheral blood mononuclear cells (PBMCs), Bal, RW/92/008/RE1 clade A and IN/2157 D15 clade C Cloning and Expression of the Paz and Laz Genes.

The laz gene from *Neisseria gonorrhoeae* was cloned based on its known sequence (SEQ ID NO: 19). The *P. aeruginosa* azurin gene (SEQ ID NO: 1), termed paz, and the sequence of the H.8 epitope of laz from *N. gonnerrhoeae* (SEQ ID NO: 18), were used to clone in frame the H.8 epitope gene in the 5'-end of paz to produce H.8-paz or in the 3'-end of paz to generate paz-H.8. See, Table 6 for bacterial strains and genetic constructs used in this and related Examples.

of EcoRI and KpnI sites are underlined respectively. The amplified DNA fragment of 1.0 kb, digested with EcoRI and KpnI, was inserted into the corresponding sites of pUC18 vector (Yanisch-Perron, et al., Gene 33:103-119 (1985)) so that the laz gene was placed downstream of the lac promoter to yield an expression plasmid pUC18-laz (Table 6).

The plasmids expressing fusion H.8 of *N. gonorrhoeae* Laz and azurin of *P. aeruginosa* (Paz) were constructed by PCR with pUC19-paz and pUC18-laz as templates. For H.8-Paz fusion, a 3.1 kb fragment was amplified with pUC18-laz as a template and primers, 5'-(phosphorylated) GGCAGCAGGGGCTTCGGCAGCATCTGC-3' (SEQ ID NO: 22) and 5'-CTGCAG GTCGACTCTAGAGGATCCCG-3' (SEQ ID NO: 23) where a SalI site is underlined. A PCR amplified a 0.4 kb fragment was obtained from pUC19-paz as a template and primers, 5'-(phosphorylated)GCCGAGTGCTCGGTGGA-CATCCAGG-3' (SEQ ID NO: 24) and 5'-TA CTCGAGTCACTTCAGGGTCAGGGTG-3' (SEQ ID NO: 25) where a XhoI site is underlined. A SalI digested PCR fragment from pUC18-laz and XhoI digested PCR fragment from pUC19-paz were cloned to yield an expression plasmid pUC18-H.8-paz (Table 6).

TABLE 6

Bacterial strains and genetic constructs

| Cells/strains/ plasmids | Relevant characteristics* | Reference |
|---|---|---|
| *P. aeruginosa* PAO1 | Prototroph, FP− (sex factor minus) | Holloway, et al., Microbiol. Rev. 43: 73-102 (1979) |
| *E. coli* JM109 | Cloning and azurin expression strain | Yanisch-Perron, et al., Gene 33: 103-119 (1985) |
| *E. coli* BL21 (DE3) | GST expression strain | Novagen |
| *N. gonorrhoeae* F62 | Prototroph used for DNA isolation | American Type Culture Collection |
| pUC18 | General cloning vector, Ap$^r$ | Yanisch-Perron, et al., id. |
| pUC19 | General cloning vector, Ap$^r$ | Yanisch-Perron, et al., id. |
| pUC18-laz | A 1 kb PCR fragment from genomic DNA of N. gonorrhoeae F62 cloned into pUC18 | Herein |
| pUC19-paz | A 0.55 kb PCR fragment from *P. aeruginosa* PAO1 cloned into HindIII and PstI digested pUC19, Ap$^r$ | Yamada, et al., Proc. Natl. Acad. Sci. USA 99: 14098-14103 (2002); Yamada, et al., Proc. Natl. Acad. Sci. USA 101: 4770-4775 (2004) |
| pUC18-H.8-paz | Fusion plasmid encoding H.8 from *N. gonorrhoeae* and azurin from *P. aeruginosa* PAO1, Ap$^r$ | Herein |
| pGEX-5X-3 | GST gene fusion vectors, Ap$^r$ | Amersham |
| pET29a | *E. coli* expression vector, Km$^r$ | Novagen |
| pET29a-gst | pET29a derivative containing the gst gene, Km$^r$ | Herein |
| pGEX-5X-3-H.8 | pGEX-5X-3 derivative containing H.8-encoding region, Ap$^r$ | Herein |
| pET29a-gst-H.8 | pET29a derivative containing gst-H.8 gene, Km$^r$ | Herein |

*Ap, ampicillin; Km, kanamycin; GST, Glutathione S-transferase.

The cloning and hyperexpression of the azurin gene has been described. (Yamada, et al., Proc. Natl. Acad. Sci. USA 99:14098-14103 (2002); Punj, et al., Oncogene 23:2367-2378 (2004)) The Laz-encoding gene (laz) of *Neisseria gonorrhoeae* was amplified by PCR with genomic DNA of *N. gonorrhoeae* strain F62 as template DNA. The forward and reverse primers used were 5'-CCG GAATTCCGGCAGGGATGTTGTAAATATCCG-3' (SEQ ID NO: 20) and 5'-GGGGTACCGC-CGTGGCAGGCATACAGCATTTCAATCGG-3' (SEQ ID NO: 21) where the additionally introduced restriction sites

*E. coli* JM109 was used as a host strain for expression of azurin and its derivative genes. Recombinant *E. coli* strains were cultivated in 2× YT medium containing 100 μg/ml ampicillin, 0.1 mM IPTG and 0.5 mM CuSO$_4$ for 16 h at 37° C. to produce the azurin proteins.

When *E. coli* strains harboring these plasmids were grown in presence of IPTG, cells lysed and the proteins purified as described for azurin (Yamada, et al., Proc. Natl. Acad. Sci. USA 99:14098-14103 (2002); Punj, et al., Oncogene 23:2367-2378 (2004); Yamada, et al., Cell. Microbiol. 7:1418-1431 (2005)), the various azurin derivatives migrated on SDS-PAGE as single components, although the H.8 containing proteins (about 17 kDa) showed anomalous migrations, as noted before. (Cannon, Clin. Microbiol. Rev. 2:S1-S4 (1989); Fisette, et al., J. Biol. Chem. 278:46252-46260 (2003))

HIV-1 Suppression Assay.

Azurin, H.8-azurin and Laz were filter sterilized through a 0.45 µM filter. Peripheral blood mononuclear cells (PBMC) were treated with polybrene (5 µg/ml) for 1 h and seeded at 250,000 cells/well in a microtiter plate. The plate was spun at 800 rpm for 5 min to collect the cells. The supernatant was taken off and media with protein (at concentrations of 0.3, 0.6, 1.2, 6.0 and 30 µM) was added (100 µl). The cells were then incubated for 1 h. AZT (25 µM) was used as a control. The proteins were left on cells and 100 µl of virus (Bal, 2167, or RW/92/008/RE1) was added and incubated for 2 h. The plate was spun again at 800 rpm for 5 minutes and protein and virus was removed. Protein and media were added back for a total volume of 100 µl and incubated for 5 days. At the end of the 5 day period, the culture supernatant was tested for HIV/p24 by ELISA.

The results in FIG. 1 show that azurin at a concentration of 6.0 µM shows about 90% suppression of the growth of HIV-1 Bal, the most predominant clade B circulating in the US and Western Europe, a clade B African isolate RW/92/008/RE1 and a clade C Indian isolate IN/2167 D15. However, H.8-azurin (azurin with the H.8 epitope in the N-terminal) had high inhibitory activity against all the three subtypes at concentrations as low as 0.3 µM, particularly for the African and the Indian subtypes (FIG. 1).

The Neisserial protein Laz, which also harbors the H.8 epitope in the N-terminal part of the Neisserial azurin homolog (Gotschlich & Seiff *FEMS Microbiol. Lett.* 43:253-255 (1987); Kawula et al., Mol. Microbiol. 1:179-185 (1987)), had similar inhibitory activity for the three subtypes, particularly for the African and the Indian subtypes (FIG. 1), demonstrating a role of the H.8 epitope in promoting enhanced anti-HIV-1 activity by azurin. No effect on host cell (PBMC) death by MTT assay (Yamada et al., Proc. Natl. Acad. Sci. USA 99:14098-14103 (2002); Punj et al., Oncogene 23:2367-2378 (2004)) was discernible for all concentrations of these three proteins, suggesting that inhibition of HIV-1 growth was not due to death of the host cells.

Example 4: Azurin Binding with gp120 and CD4 as Studied by Surface Plasmon Resonance Surface Plasmon Resonance experiments were conducted to determine the extent of azurin binding not only to CD4 but also to HIV-1 surface proteins such as gp120 or gp41 known to be involved in HIV-1 entry and other proteins such as Nef or Gag that are involved in intracellular virus multiplication.

Plasmid Construction for Fusion GST Proteins.

Plasmids expressing fusion glutathione S-transferase (GST)-truncated wt-azurin (azu) derivatives were constructed by a polymerase chain reaction using proofreading DNA polymerase. For pGST-azu 36-128, an amplified PCR fragment was introduced into the BamH1 and EcoR1 sites of the commercial GST expression vector pGEX-5X (Amersham Biosciences, Piscataway, N.J.). The fragment was amplified with pUC19-azu as a template and primers, 5'-C<u>GGGATCC</u> CCG GCA ACC TGC CGA AGA TCA TGG GC-3' (SEQ ID NO: 26) and 5'-CGG<u>GAATTC</u> GCA TCA CTT CAG GGT CAG GG-3' (SEQ ID NO: 27), where the additionally introduced BamH1 and EcoR1 sites are underlined respectively. Carboxyl-terminus truncation of azu gene was cumulatively performed by introducing a stop codon using QuickChange site-direct mutagenesis kit (Stratagene, La Jolla, Calif.).

For pGST-azu 36-89, a stop codon were introduced into Gly90. The plasmid carrying pGST-azu 36-128 was used as template DNA. Three sets of oligonucleotides for site-direct mutagenesis are shown as follows. For pGST-azu 36-89: 5'-CCA AGC TGA TCG GCT CGT GAG AGAAGG ACT CGG TGA CC-3' (SEQ ID NO: 28), and 5'-GGT CAC CGA GTC CTT CTC TCA CGA GCC GAT CAG CTT GG-3 (SEQ ID NO: 29).

For pGST-azu 88-113, carboxyl terminus truncation of azu gene was cumulatively performed by introducing stop codon using QuickChange site directed mutagenesis kit (Stratagene, La Jolla, Calif.). For pGST-azu 88-113, a stop codon was introduced into Phe114. The plasmid carrying pGST-azu 88-128 was used as the template. For pGST-azu 88-128 an amplified PCR fragment was introduced into the BamH1 and EcoR1 sites of the commercial GST expression vector pGEX-5X (Amersham Biosciences). The fragment was amplified with pUC19-azu as the template and primers, 5'-C<u>GGGGATCC</u> CCG GCT CGG GCG AGA AGG AC-3' (SEQ ID NO: 30) and 5'-CGG<u>GAATTC</u> TCC ACT TCA GGG TCA GGG TG-3' (SEQ ID NO: 31) where the additionally introduced BamH1 and EcoR1 sites are underlined respectively.

One set of oligonucleotides for site directed mutagenesis are shown as follows for the preparation of pGST-azu 88-113: 5'-GTT CTT CTG CAC CTA GCC GGG CCA CTC CG-3' (SEQ ID NO: 32) and 5'-CGG AGT GGC CCG GCT AGG TGC AGA AGA AC-3' (SEQ ID NO: 33). pGST-azu 88-113 was used to transform *E. coli* XL-1 Blue strains. Plasmid extraction was performed using a commercial kit (Qiagen, Venlo, The Netherlands) and PCR sequencing were performed to assess plasmid insertion and transfection.

*E. coli* BL21 (DE3) was used as a host strain for expression of the gst and its fusions derivatives. *E. coli* strain XL1-Blue transformed with pGST-azu plasmids was grown in LB media with ampicillin for three hours at 37° C. upon which IPTG induction (0.4 mM) was performed an subsequent incubation for 2-4 h at 37° C. to maximize the expression levels. Cells were isolated by centrifugation, resuspended in 25 mL of 1×PBS buffer. Subsequent cell lysis involved two sequential treatments of the cell suspension via sonication (20 min on ice) and heat-cold shock in acetone-dry ice bath (using the appropriate protease inhibitors). Supernatants of the cell lysis mixture were isolated and passed through a freshly packed and PBS equilibrated 1 mL glutathione-sepharose 4B (Amersham Biosciences) column. After column washing and subsequent elution of GST-azu product using 10 mM glutathione in 20 mM Tris-HCl pH 8. GST-Azu 88-113 purity was tested via electrophoresis using a 10% SDS-PAGE Tris-Gly gel stained with Coomassie Brilliant Blue R reagent. Protein concentration was determined using the Bradford Method.

Surface Plasmon Resonance (SPR) Studies.

In vitro protein-protein interactions were evaluated using a Biacore X spectrometer from Biacore AB International (Uppsala, Sweden). All experiments were conducted at 25° C. in HBS-EP running buffer (0.01 M HEPES, pH 7.4, 0.15 M NaCl, 3 mM EDTA, 0.005% v/v Surfactant P20)) using Au-CM5 sensor chips purchased from Biacore. Protein stock solutions were prepared in PBS after desalting on G-75 column and lyophilization in order to preconcentrate and exchange the buffer.

Protein immobilizations on CM5 chips were conducted according to the amine coupling procedure. Due to differences in protein crosslinking efficiencies, proteins were immobilized under various conditions after NHS/EDC preactivation of the CM5 surface: 50 μl injections of azurin (510 μM), or 35 μl injections of CD4 (25 μM, 2×), or HIV-1 gp120 (10 μM). Subsequent treatment of CM5 surface with ethanolamine (1M, pH 8.8) removed uncrosslinked proteins prior to binding studies. Binding studies were performed by injecting protein eluents (50 μl) over the protein-CM5 surface at flow rates of 30 μl/min with a 120 sec time delay at the end of the injections. Protein eluents included CD4 (Protein Sciences Corp., Meriden, Conn.), HIV-1 gp120 (Immunodiagnostics Inc., Woburn, Mass.), HIV-1 gp41 (Bioclone Inc., San Diego, Calif.), HIV-1 gag and HIV-1-nef (Chemicon International, Temecula, Calif.) and GST-azurin fusion proteins (GST, GST-Azu 36-128, GST-Azu 36-89, and GST-Azu 88-113, expressed in inventor's laboratory). Sensor chip surfaces were regenerated between protein injections using 100 mM NaOH (10 μl injection pulse). All binding studies were run against a negative flow channel containing bare Au-CM5 to correct for nonspecific binding effects. For the binding experiments wherein CD4 and HIV-1 gp120 served as the eluents (not immobilized), 1 mg/mL of carboxymethyldextran (CarboMer Inc., San Diego Calif.) was added to the running buffer in order to reduce nonspecific protein binding to the bare Au-CM5 flow channel surface.

To generate binding constant data, titration experiments were designed via injection of increasing concentrations of protein eluents (0.05-2000 nM) and the data collected. The SPR data could be fit to a Langmuir equilibrium binding model [Req=Rmax/(1+Kd/C] form which binding constants (Kd) were determined. Similar to the binding constant studies described above, competition studies with CD4-CM5 were performed using similar protocols but with injections of HIV-1 gp120+ the competitor proteins (azurin, GST-Azu 36-128 and GST-Azu 88-113).

With CD4 immobilized in the sensor chip, both azurin and gp120 showed significant binding to CD4 (FIG. 2A). Azurin demonstrated a higher affinity for binding CD4 (Kd=36.9 nM) than the HIV-1 ligand gp120 (Kd=48.1 nM). While a GST-azurin fusion such as GST-Azu 88-113 showed no binding (FIG. 2A), another GST-azurin fusion protein, GST-Azu 36-128 showed even stronger binding than azurin itself with a Kd value of 0.34 nM (FIG. 4A inset), suggesting that parts of azurin might retain a stronger binding affinity than the full length protein. When azurin was immobilized on the sensor chip, gp120 showed somewhat stronger binding to azurin than CD4 (FIG. 2B), clearly demonstrating that azurin binds both to gp120 and CD4 with a high affinity. Interestingly, gp41, also involved in HIV-1 entry into the host cell, did not show any binding to azurin (FIG. 2B). Similar lack of binding was demonstrated for Gag and Nef.

Example 5: Azurin Binding with ICAMs and CD5 as Studied by Surface Plasmon Resonance There is a structural similarity between azurin and ICAMs (Table 5) that are known to be involved as receptors HIV-1 infections. (Liao et al., AIDS Res. Hum. Retroviruses 16:355-366 (2000); Hioe et al., J. Virol. 75:1077-1082 (2001)) ICAM-3 has been implicated in stimulating HIV-1 transcription and viral production, thereby contributing additionally to intracellular viral growth. (Barat et al., J. Virol. 78, 6692-6697 (2004))

Protein-protein interactions as measured by SPR between azurin and ICAMs such as ICAM-1, ICAM-2, ICAM-3 and NCAM were therefore studied. With immobilized azurin on the CM5 chip, ICAM-3 (FIG. 2C, $K_d$=19.5±5.4 nM) and NCAM (FIG. 2C, inset), but not ICAM-1 and ICAM-2, showed strong binding. While not limiting the operation of the invention to any one mechanism, part of azurin suppression of HIV-1 growth might also be mediated through its interaction with ICAM-3 or NCAM.

Example 6: Azurin Competition with gp120 for CD4 as Studied by Surface Plasmon Resonance Due to the higher affinity of binding of azurin to CD4, as compared to gp120 (FIG. 2A), a competition experiment was performed to see if azurin can interfere in gp120 binding with its cognate receptor CD4. As the concentration of the competitor protein (azurin, GST-Azu 36-128 or GST-Azu 88-113) was increased in presence of a fixed concentration of gp120 adsorbed to the immobilized CD4 chip, both azurin and GST-Azu 36-128 demonstrated significant decrease in the total protein binding of gp120 from the CD4-CM5 chip (FIG. 2D). Such apparent displacement of gp120 from the chip was not observed in case of GST-Azu 88-113 (FIG. 2D). GST-Azu 88-113 is known not to bind CD4 (FIG. 2A). While not limiting the operation of the invention to any one mechanism, this indicates that azurin or GST-Azu 36-128 fusion protein may successfully inhibit the complex formation between gp120 and CD4.

Example 7: Azurin and ICAM-3 Binding with DC-SIGN as Studied by Surface Plasmon Resonance The strong binding of azurin with gp120, CD4 and ICAM-3 (FIG. 2) mimics the binding of another very important HIV-1 binding protein present on the surface of dendritic cells (DC) known as DC-SIGN (DC-specific intercellular adhesion molecule 3-grabbing nonintegrin) and a related protein called DC-SIGN/R. DC-SIGN is expressed abundantly on DC while DC-SIGN/R is expressed primarily on sinusoidal and endothelial cells. DC-SIGN plays a major role in HIV-1 immunopathogenesis by allowing DC, which are professional antigen presenting cells, to capture and present pathogens including HIV-1 to resting T cells through their interactions with ICAM-3 on the T cell surface. (Geijtenbeek et al., Cell 100, 575-585 (2000); Soilleux, Clin. Sci. 104, 437-446 (2003); Geijtenbeek et al., Placenta 22, S19-S23 (2001)). DC-SIGN has also been shown to bind avidly to HIV-1 envelope protein gp120, thereby capturing HIV-1 and transporting it to CD4+ T cells, where HIV-1 can replicate freely. (Snyder et al., J. Virol. 79:4589-4598 (2005))

Figure 3:
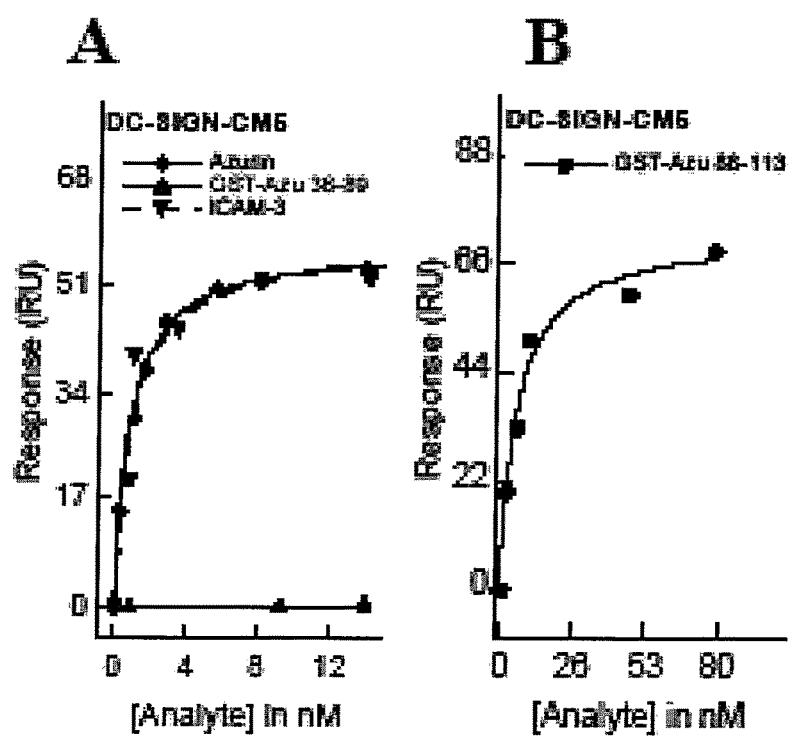
FIG. 3 depicts surface plasmon resonance binding titrations depicting the interactions of azurin, and GST-Azurin fusions with DC-SIGN. (A) Concentration dependent binding of azurin, ICAM-3, and GST-Azu 36-89 with DC-SIGN were determined via injection of various concentrations of the proteins (0-100 nM) over a DC-SIGN modified CM5 sensor surface and the extent of binding was evaluated as a function of the equilibrium resonance response value measured in resonance units (RU). (B) The binding titration curve of GST-Azu 88-113 with DC-SIGN using the same sensor chip and protocol as described for azurin in part A. The positive interaction of GST-Azu 88-113 with DC-SIGN suggests its potential role as the recognition sequence for azurin. The binding affinities (Kd) for azurin, ICAM-3 and GST-Azu 88-113 were determined by fitting the data to Req=Rmax/(1+(Kd/C)) and the curve fits connect the data points in these plots. The extrapolated Kd values are 0.83±0.05 nM (azurin), 0.93±0.39 nM (ICAM-3), and 5.98±1.13 nM (GST-Azu 88-113).

In SPR experiments with immobilized DC-SIGN on the sensor chip, both azurin ($K_d$=0.83±0.05 nM) and ICAM-3 ($K_d$=0.93±0.39 nM) bound strongly to DC-SIGN (FIG. 3A). While the GST-fusion derivative GST-Azu 36-89 showed very little binding (FIG. 3A), another GST-fusion derivative GST-Azu 88-113 exhibited relatively strong binding ($K_d$=5.98±1.13 nM), demonstrating the involvement of the C-terminal part of azurin in DC-SIGN binding (FIG. 3B). GST-Azu 88-113, however, does not bind with CD4 (FIG. 2A), suggesting that different parts of azurin have different binding specificities.

While not limiting the operation of the invention to any one mechanism, such binding with DC-SIGN demonstrates azurin's potential ability to interfere in the binding of HIV-1 with DCs. Thus DC-SIGN, a critical molecule on DC surface responsible for transmitting HIV-1 from the mucosal cells to the lymphoid T cells, may well find a strong competitor in azurin or Laz that can also avidly bind gp120, CD4 and ICAM-3.

Example 8: Azurin/Laz Acts in the Entry Stage of HIV-1 Infection

To determine if azurin acts at the entry or post entry step of HIV-1 infection, the effect of Laz on the Indian isolate IN/2167 of HIV-1 was investigated. In one experiment, activated PBMC (25,000 cells/well) were incubated with 6.0 µM Laz and HIV-1 for 2 h. The mixture was centrifuged to remove Laz and HIV-1, fresh medium without Laz was added back, and the culture was grown for 5 days. HIV-1 growth was monitored by measurement of p24 in the culture supernatant. Under this condition, Laz (6.0 µM) suppressed the HIV-1 growth by 43%. With higher concentration of Laz (30 µM), the extent of suppression was 76%. In a parallel experiment, when the Laz (6 or 30 µM) was added to the PBMC after the HIV-1 infection and its removal, very little suppression of viral growth was observed. As a positive control, when Laz (6.0 µM) was present both during infection and after removal of the virus with fresh medium during 5 days of the culture, the extent of inhibition was about 93%. While not limiting the operation of the invention to any one mechanism. such data clearly indicate that azurin or Laz exerts its effect primarily at the entry stage of infection.

Example 9: Treatment of HIV-Infected Patients with Azurin

Twenty four patients with AIDS presents with low to non-detectable HIV viral loads (RNA PCR) in the plasma as measured by PCR techniques, and increased CD4+ counts. Next, CD4+RO+ cells are enriched by magnetic separation and FACS sorting, and assayed to determine infectivity with respect to naive and uninfected cell co-culture experiments. This analysis of CD4+RO+ memory cells shows the presence of infective HIV.

Azurin is therefore administered to twenty of the patients at a dose of 4 mg/m$^2$ by intravenous infusion once every two weeks for a period of 3 months until CD4+ cells, including memory cells, are at low levels. Four patients receive placebo infusions. During administration of azurin and for a period of approximately 1-2 months thereafter, or until CD4+ cells recover, the patients are maintained with antibiotics and antifungal therapy. Stem cell or precursor cell replacement is provided through a bone marrow transplant and cytokine therapy, both of which are performed according to conventional techniques.

During and following therapy, the patients are followed at frequent intervals and monitored for CD34 cell level, reestablishment of CD4+ cells and quantitation of CD4+RO+ cells. Additionally, the patients' plasma is assayed for viral load by cell co-culture experiments. On reducing virus load in active and memory CD4+ T cells to low or non-detectable concentrations, the patients are weaned from azurin. After 3 months, the patients are weaned from antibiotic and antifungal therapy. Following this, the patients are followed at 6 month intervals and assayed for viral content. The results demonstrate the effectiveness of azurin therapy for patients with HIV infection.

What is claimed:

1. A pharmaceutical composition comprising:
   at least two different polypeptides, a first polypeptide comprising a cytochrome C551; and
   a second polypeptide consisting of an amino acid sequence selected from the group consisting of: residues 36-128 of SEQ ID NO: 1, residues 36-88 of SEQ ID NO: 1, residues 88-113 of SEQ ID NO: 1, and a fusion of residues 36-128 of SEQ ID NO: 1 and SEQ ID NO: 18; and
   a pharmaceutically-acceptable carrier;
   wherein at least one of the first and second polypeptides has been modified by one or more of amidation, acetylation, sulfation, polyethylene glycol (PEG) modification, phosphorylation, glycosylation, substitution of an amino acid, deletion of an amino acid or insertion of an amino acid.

2. The pharmaceutical composition of claim 1, wherein one of the at least two different polypeptides is capable of binding to one or more targets selected from the group consisting of: CD4, gp120, ICAM-3, and DC-SIGN.

3. The pharmaceutical composition of claim 1, further comprising a drug molecule, a therapeutic agent, a pharmaceutical agent, another polypeptide, or a detectable probe, wherein one of the at least two different polypeptides is fused to the drug molecules.

4. A pharmaceutical composition comprising:
   one peptide consisting of an amino acid sequence selected from the group consisting of: residues 36-128 of SEQ ID NO: 1, residues 36-88 of SEQ ID NO: 1, and residues 88-113 of SEQ ID NO: 1; and
   a pharmaceutically-acceptable carrier;
   wherein the one peptide is modified by one or more of amidation, acetylation, sulfation, polyethylene glycol (PEG) modification, phosphorylation, glycosylation, substitution of an amino acid, deletion of an amino acid, or insertion of an amino acid.

5. The pharmaceutical composition of claim 4, wherein the one peptide is capable of binding to one or more targets selected from the group consisting of CD4, gp120, ICAM-3, and DC SIGN.

6. A pharmaceutical composition comprising:
a first peptide consisting of the amino acid sequence of SEQ ID NO: 1;
a second peptide comprising a cytochrome C551; and
a pharmaceutically-acceptable carrier;
wherein the first peptide and the second peptide are different and
wherein the first or second peptide or both is/are modified by one or more of amidation, acetylation, sulfation, polyethylene glycol (PEG) modification, phosphorylation, glycosylation, substitution of an amino acid, deletion of an amino acid, or insertion of an amino acid.

7. The pharmaceutical composition of claim 6, wherein the second peptide consists of SEQ ID NO: 2.

\* \* \* \* \*

SEQUENCE LISTING

```
<160> NUMBER OF SEQ ID NOS: 33

<210> SEQ ID NO 1
<211> LENGTH: 128
<212> TYPE: PRT
<213> ORGANISM: Pseudomonas aeruginosa

<400> SEQUENCE: 1

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
        115                 120                 125

<210> SEQ ID NO 2
<211> LENGTH: 82
<212> TYPE: PRT
<213> ORGANISM: Pseudomonas aeruginosa
```

```
<400> SEQUENCE: 2

Glu Asp Pro Glu Val Leu Phe Lys Asn Lys Gly Cys Val Ala Cys His
1               5                   10                  15

Ala Ile Asp Thr Lys Met Val Gly Pro Ala Tyr Lys Asp Val Ala Ala
            20                  25                  30

Lys Phe Ala Gly Gln Ala Gly Ala Glu Ala Glu Leu Ala Gln Arg Ile
        35                  40                  45

Lys Asn Gly Ser Gln Gly Val Trp Gly Pro Ile Pro Met Pro Pro Asn
    50                  55                  60

Ala Val Ser Asp Asp Glu Ala Gln Thr Leu Ala Lys Trp Val Leu Ser
65                  70                  75                  80

Gln Lys

<210> SEQ ID NO 3
<211> LENGTH: 105
<212> TYPE: PRT
<213> ORGANISM: Phormidium laminosum

<400> SEQUENCE: 3

Glu Thr Phe Thr Val Lys Met Gly Ala Asp Ser Gly Leu Leu Gln Phe
1               5                   10                  15

Glu Pro Ala Asn Val Thr Val His Pro Gly Asp Thr Val Lys Trp Val
            20                  25                  30

Asn Asn Lys Leu Pro Pro His Asn Ile Leu Phe Asp Asp Lys Gln Val
        35                  40                  45

Pro Gly Ala Ser Lys Glu Leu Ala Asp Lys Leu Ser His Ser Gln Leu
    50                  55                  60

Met Phe Ser Pro Gly Glu Ser Tyr Glu Ile Thr Phe Ser Ser Asp Phe
65                  70                  75                  80

Pro Ala Gly Thr Tyr Thr Tyr Tyr Cys Ala Pro His Arg Gly Ala Gly
                85                  90                  95

Met Val Gly Lys Ile Thr Val Glu Gly
            100                 105

<210> SEQ ID NO 4
<211> LENGTH: 155
<212> TYPE: PRT
<213> ORGANISM: Thiobacillus ferrooxidans

<400> SEQUENCE: 4

Gly Thr Leu Asp Thr Thr Trp Lys Glu Ala Thr Leu Pro Gln Val Lys
1               5                   10                  15

Ala Met Leu Glu Lys Asp Thr Gly Lys Val Ser Gly Asp Thr Val Thr
            20                  25                  30

Tyr Ser Gly Lys Thr Val His Val Val Ala Ala Val Leu Pro Gly Gly
        35                  40                  45

Phe Pro Phe Pro Ser Phe Glu Val His Asp Lys Lys Asn Pro Thr Leu
    50                  55                  60

Glu Ile Pro Ala Gly Ala Thr Val Asp Val Thr Phe Ile Asn Thr Asn
65                  70                  75                  80

Lys Gly Phe Gly His Ser Phe Asp Ile Thr Lys Lys Gly Pro Pro Tyr
                85                  90                  95

Ala Val Met Pro Val Ile Asp Pro Ile Val Ala Gly Thr Gly Phe Ser
                100                 105                 110

Pro Val Pro Lys Asp Gly Lys Phe Gly Tyr Thr Asp Phe Thr Trp His
```

```
                115                 120                 125
Pro Thr Ala Gly Thr Tyr Tyr Tyr Val Cys Gln Ile Pro Gly His Ala
            130                 135                 140

Ala Thr Gly Met Phe Gly Lys Ile Val Val Lys
145                 150                 155

<210> SEQ ID NO 5
<211> LENGTH: 124
<212> TYPE: PRT
<213> ORGANISM: Achromabacter cycloclastes

<400> SEQUENCE: 5

Ala Asp Phe Glu Val His Met Leu Asn Lys Gly Lys Asp Gly Ala Met
1               5                   10                  15

Val Phe Glu Pro Ala Ser Leu Lys Val Ala Pro Gly Asp Thr Val Thr
            20                  25                  30

Phe Ile Pro Thr Asp Lys Gly His Asn Val Glu Thr Ile Lys Gly Met
        35                  40                  45

Ile Pro Asp Gly Ala Glu Ala Phe Lys Ser Lys Ile Asn Glu Asn Tyr
    50                  55                  60

Lys Val Thr Phe Thr Ala Pro Gly Val Tyr Gly Val Lys Cys Thr Pro
65                  70                  75                  80

His Tyr Gly Met Gly Met Val Gly Val Gln Val Gly Asp Ala Pro
                85                  90                  95

Ala Asn Leu Glu Ala Val Lys Gly Ala Lys Asn Pro Lys Lys Ala Gln
            100                 105                 110

Glu Arg Leu Asp Ala Ala Leu Ala Ala Leu Gly Asn
            115                 120

<210> SEQ ID NO 6
<211> LENGTH: 128
<212> TYPE: PRT
<213> ORGANISM: Alcaligenes faecalis

<400> SEQUENCE: 6

Ala Cys Asp Val Ser Ile Glu Gly Asn Asp Ser Met Gln Phe Asn Thr
1               5                   10                  15

Lys Ser Ile Val Val Asp Lys Thr Cys Lys Glu Phe Thr Ile Asn Leu
            20                  25                  30

Lys His Thr Gly Lys Leu Pro Lys Ala Ala Met Gly His Asn Val Val
        35                  40                  45

Val Ser Lys Lys Ser Asp Glu Ser Ala Val Ala Thr Asp Gly Met Lys
    50                  55                  60

Ala Gly Leu Asn Asn Asp Tyr Val Lys Ala Gly Asp Glu Arg Val Ile
65                  70                  75                  80

Ala His Thr Ser Val Ile Gly Gly Gly Glu Thr Asp Ser Val Thr Phe
                85                  90                  95

Asp Val Ser Lys Leu Lys Glu Gly Glu Asp Tyr Ala Phe Phe Cys Ser
            100                 105                 110

Phe Pro Gly His Trp Ser Ile Met Lys Gly Thr Ile Glu Leu Gly Ser
            115                 120                 125

<210> SEQ ID NO 7
<211> LENGTH: 129
<212> TYPE: PRT
<213> ORGANISM: Achromobacter xylosoxidans

<400> SEQUENCE: 7
```

```
Ala Gln Cys Glu Ala Thr Ile Glu Ser Asn Asp Ala Met Gln Tyr Asn
1               5                   10                  15

Leu Lys Glu Met Val Val Asp Lys Ser Cys Lys Gln Phe Thr Val His
            20                  25                  30

Leu Lys His Val Gly Lys Met Ala Lys Val Ala Met Gly His Asn Trp
            35                  40                  45

Val Leu Thr Lys Glu Ala Asp Lys Gln Gly Val Ala Thr Asp Gly Met
        50                  55                  60

Asn Ala Gly Leu Ala Gln Asp Tyr Val Lys Ala Gly Asp Thr Arg Val
65                  70                  75                  80

Ile Ala His Thr Lys Val Ile Gly Gly Gly Ser Asp Ser Val Thr
                85                  90                  95

Phe Asp Val Ser Lys Leu Thr Pro Gly Glu Ala Tyr Ala Tyr Phe Cys
                100                 105                 110

Ser Phe Pro Gly His Trp Ala Met Met Lys Gly Thr Leu Lys Leu Ser
            115                 120                 125

Asn
```

<210> SEQ ID NO 8
<211> LENGTH: 129
<212> TYPE: PRT
<213> ORGANISM: Bordetella bronchiseptica

<400> SEQUENCE: 8

```
Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr Val Asn
            20                  25                  30

Leu Lys His Thr Gly Lys Leu Pro Arg Asn Val Met Gly His Asn Trp
            35                  40                  45

Val Leu Thr Lys Thr Ala Asp Met Gln Ala Val Glu Lys Asp Gly Ile
        50                  55                  60

Ala Ala Gly Leu Asp Asn Gln Tyr Leu Lys Ala Gly Asp Thr Arg Val
65                  70                  75                  80

Leu Ala His Thr Lys Val Leu Gly Gly Gly Glu Ser Asp Ser Val Thr
                85                  90                  95

Phe Asp Val Ala Lys Leu Ala Ala Gly Asp Tyr Thr Phe Phe Cys
                100                 105                 110

Ser Phe Pro Gly His Gly Ala Leu Met Lys Gly Thr Leu Lys Leu Val
            115                 120                 125

Asp
```

<210> SEQ ID NO 9
<211> LENGTH: 129
<212> TYPE: PRT
<213> ORGANISM: Methylomonas sp.

<400> SEQUENCE: 9

```
Ala Ser Cys Glu Thr Thr Val Thr Ser Gly Asp Thr Met Thr Tyr Ser
1               5                   10                  15

Thr Arg Ser Ile Ser Val Pro Ala Ser Cys Ala Glu Phe Thr Val Asn
            20                  25                  30

Phe Glu His Lys Gly His Met Pro Lys Thr Gly Met Gly His Asn Trp
            35                  40                  45

Val Leu Ala Lys Ser Ala Asp Val Gly Asp Val Ala Lys Glu Gly Ala
```

```
                  50                  55                  60
His Ala Gly Ala Asp Asn Asn Phe Val Thr Pro Gly Asp Lys Arg Val
 65                  70                  75                  80

Ile Ala Phe Thr Pro Ile Ile Gly Gly Glu Lys Thr Ser Val Lys
                 85                  90                  95

Phe Lys Val Ser Ala Leu Ser Lys Asp Glu Ala Tyr Thr Tyr Phe Cys
                100                 105                 110

Ser Tyr Pro Gly His Phe Ser Met Met Arg Gly Thr Leu Lys Leu Glu
                115                 120                 125

Glu

<210> SEQ ID NO 10
<211> LENGTH: 166
<212> TYPE: PRT
<213> ORGANISM: Neisseria meningitidis

<400> SEQUENCE: 10

Cys Ser Gln Glu Pro Ala Ala Pro Ala Ala Glu Ala Thr Pro Ala Ala
  1               5                  10                  15

Glu Ala Pro Ala Ser Glu Ala Pro Ala Ala Glu Ala Ala Pro Ala Asp
                 20                  25                  30

Ala Ala Glu Ala Pro Ala Ala Gly Asn Cys Ala Ala Thr Val Glu Ser
                 35                  40                  45

Asn Asp Asn Met Gln Phe Asn Thr Lys Asp Ile Gln Val Ser Lys Ala
 50                  55                  60

Cys Lys Glu Phe Thr Ile Thr Leu Lys His Thr Gly Thr Gln Pro Lys
 65                  70                  75                  80

Thr Ser Met Gly His Asn Ile Val Ile Gly Lys Thr Glu Asp Met Asp
                 85                  90                  95

Gly Ile Phe Lys Asp Gly Val Gly Ala Ala Asp Thr Asp Tyr Val Lys
                100                 105                 110

Pro Asp Asp Ala Arg Val Val Ala His Thr Lys Leu Ile Gly Gly Gly
                115                 120                 125

Glu Glu Ser Ser Leu Thr Leu Asp Pro Ala Lys Leu Ala Asp Gly Glu
                130                 135                 140

Tyr Lys Phe Ala Cys Thr Phe Pro Gly His Gly Ala Leu Met Asn Gly
145                 150                 155                 160

Lys Val Thr Leu Val Asp
                165

<210> SEQ ID NO 11
<211> LENGTH: 128
<212> TYPE: PRT
<213> ORGANISM: Pseudomomas fluorescens

<400> SEQUENCE: 11

Ala Glu Cys Lys Thr Thr Ile Asp Ser Thr Asp Gln Met Ser Phe Asn
  1               5                  10                  15

Thr Lys Ala Ile Glu Ile Asp Lys Ala Cys Lys Thr Phe Thr Val Glu
                 20                  25                  30

Leu Thr His Ser Gly Ser Leu Pro Lys Asn Val Met Gly His Asn Leu
                 35                  40                  45

Val Ile Ser Lys Gln Ala Asp Met Gln Pro Ile Ala Thr Asp Gly Leu
                 50                  55                  60

Ser Ala Gly Ile Asp Lys Asn Tyr Leu Lys Glu Gly Asp Thr Arg Val
 65                  70                  75                  80
```

-continued

```
Ile Ala His Thr Lys Val Ile Gly Ala Gly Glu Lys Asp Ser Leu Thr
                85                  90                  95

Ile Asp Val Ser Lys Leu Asn Ala Ala Glu Lys Tyr Gly Phe Phe Cys
            100                 105                 110

Ser Phe Pro Gly His Ile Ser Met Met Lys Gly Thr Val Thr Leu Lys
        115                 120                 125

<210> SEQ ID NO 12
<211> LENGTH: 128
<212> TYPE: PRT
<213> ORGANISM: Pseudomonas chlororaphis

<400> SEQUENCE: 12

Ala Glu Cys Lys Val Asp Val Asp Ser Thr Asp Gln Met Ser Phe Asn
1               5                   10                  15

Thr Lys Glu Ile Thr Ile Asp Lys Ser Cys Lys Thr Phe Thr Val Asn
            20                  25                  30

Leu Thr His Ser Gly Ser Leu Pro Lys Asn Val Met Gly His Asn Trp
        35                  40                  45

Val Leu Ser Lys Ser Ala Asp Met Ala Gly Ile Ala Thr Asp Gly Met
    50                  55                  60

Ala Ala Gly Ile Asp Lys Asp Tyr Leu Lys Pro Gly Asp Ser Arg Val
65                  70                  75                  80

Ile Ala His Thr Lys Ile Ile Gly Ser Gly Glu Lys Asp Ser Val Thr
                85                  90                  95

Phe Asp Val Ser Lys Leu Thr Ala Gly Glu Ser Tyr Glu Phe Phe Cys
            100                 105                 110

Ser Phe Pro Gly His Asn Ser Met Met Lys Gly Ala Val Val Leu Lys
        115                 120                 125

<210> SEQ ID NO 13
<211> LENGTH: 129
<212> TYPE: PRT
<213> ORGANISM: Xylella fastidiosa

<400> SEQUENCE: 13

Lys Thr Cys Ala Val Thr Ile Ser Ala Asn Asp Gln Met Lys Phe Asp
1               5                   10                  15

Gln Asn Thr Ile Lys Ile Ala Ala Glu Cys Thr His Val Asn Leu Thr
            20                  25                  30

Leu Thr His Thr Gly Lys Lys Ser Ala Arg Val Met Gly His Asn Trp
        35                  40                  45

Val Leu Thr Lys Thr Thr Asp Met Gln Ala Val Ala Leu Ala Gly Leu
    50                  55                  60

His Ala Thr Leu Ala Asp Asn Tyr Val Pro Lys Ala Asp Pro Arg Val
65                  70                  75                  80

Ile Ala His Thr Ala Ile Ile Gly Gly Gly Glu Arg Thr Ser Ile Thr
                85                  90                  95

Phe Pro Thr Asn Thr Leu Ser Lys Asn Val Ser Tyr Thr Phe Phe Cys
            100                 105                 110

Ser Phe Pro Gly His Trp Ala Leu Met Lys Gly Thr Leu Asn Phe Gly
        115                 120                 125

Gly

<210> SEQ ID NO 14
<211> LENGTH: 138
```

<212> TYPE: PRT
<213> ORGANISM: Cucumis sativus

<400> SEQUENCE: 14

Met Gln Ser Thr Val His Ile Val Gly Asp Asn Thr Gly Trp Ser Val
1               5                   10                  15

Pro Ser Ser Pro Asn Phe Tyr Ser Gln Trp Ala Ala Gly Lys Thr Phe
            20                  25                  30

Arg Val Gly Asp Ser Leu Gln Phe Asn Phe Pro Ala Asn Ala His Asn
        35                  40                  45

Val His Glu Met Glu Thr Lys Gln Ser Phe Asp Ala Cys Asn Phe Val
    50                  55                  60

Asn Ser Asp Asn Asp Val Glu Arg Thr Ser Pro Val Ile Glu Arg Leu
65                  70                  75                  80

Asp Glu Leu Gly Met His Tyr Phe Val Cys Thr Val Gly Thr His Cys
                85                  90                  95

Ser Asn Gly Gln Lys Leu Ser Ile Asn Val Ala Ala Asn Ala Thr
            100                 105                 110

Val Ser Met Pro Pro Ser Ser Pro Pro Ser Ser Val Met Pro
        115                 120                 125

Pro Pro Val Met Pro Pro Ser Pro Ser
    130                 135

<210> SEQ ID NO 15
<211> LENGTH: 162
<212> TYPE: PRT
<213> ORGANISM: Chloroflexus aurantiacus

<400> SEQUENCE: 15

Met Lys Ile Thr Leu Arg Met Val Leu Ala Val Leu Thr Ala Met
1               5                   10                  15

Ala Met Val Leu Ala Ala Cys Gly Gly Gly Ser Ser Gly Gly Ser
            20                  25                  30

Thr Gly Gly Gly Ser Gly Ser Gly Pro Val Thr Ile Glu Ile Gly Ser
        35                  40                  45

Lys Gly Glu Glu Leu Ala Phe Asp Lys Thr Glu Leu Thr Val Ser Ala
    50                  55                  60

Gly Gln Thr Val Thr Ile Arg Phe Lys Asn Asn Ser Ala Val Gln Gln
65                  70                  75                  80

His Asn Trp Ile Leu Val Lys Gly Gly Glu Ala Glu Ala Ala Asn Ile
                85                  90                  95

Ala Asn Ala Gly Leu Ser Ala Gly Pro Ala Ala Asn Tyr Leu Pro Ala
            100                 105                 110

Asp Lys Ser Asn Ile Ile Ala Glu Ser Pro Leu Ala Asn Gly Asn Glu
        115                 120                 125

Thr Val Glu Val Thr Phe Thr Ala Pro Ala Ala Gly Thr Tyr Leu Tyr
    130                 135                 140

Ile Cys Thr Val Pro Gly His Tyr Pro Leu Met Gln Gly Lys Leu Val
145                 150                 155                 160

Val Asn

<210> SEQ ID NO 16
<211> LENGTH: 140
<212> TYPE: PRT
<213> ORGANISM: Chloroflexus aurantiacus

<400> SEQUENCE: 16

```
Ala Ala Asn Ala Pro Gly Gly Ser Asn Val Val Asn Glu Thr Pro Ala
1               5                   10                  15

Gln Thr Val Glu Val Arg Ala Ala Pro Asp Ala Leu Ala Phe Ala Gln
            20                  25                  30

Thr Ser Leu Ser Leu Pro Ala Asn Thr Val Val Arg Leu Asp Phe Val
        35                  40                  45

Asn Gln Asn Asn Leu Gly Val Gln His Asn Trp Val Leu Val Asn Gly
    50                  55                  60

Gly Asp Asp Val Ala Ala Val Asn Thr Ala Ala Gln Asn Asn Ala
65              70                  75                  80

Asp Ala Leu Phe Val Pro Pro Asp Thr Pro Asn Ala Leu Ala Trp
                85                  90                  95

Thr Ala Met Leu Asn Ala Gly Glu Ser Gly Ser Val Thr Phe Arg Thr
            100                 105                 110

Pro Ala Pro Gly Thr Tyr Leu Tyr Ile Cys Thr Phe Pro Gly His Tyr
            115                 120                 125

Leu Ala Gly Met Lys Gly Thr Leu Thr Val Thr Pro
            130                 135                 140
```

<210> SEQ ID NO 17
<211> LENGTH: 96
<212> TYPE: PRT
<213> ORGANISM: Cucumis sativus

<400> SEQUENCE: 17

```
Ala Val Tyr Val Val Gly Gly Ser Gly Gly Trp Thr Phe Asn Thr Glu
1               5                   10                  15

Ser Trp Pro Lys Gly Lys Arg Phe Arg Ala Gly Asp Ile Leu Leu Phe
            20                  25                  30

Asn Tyr Asn Pro Ser Met His Asn Val Val Val Val Asn Gln Gly Gly
        35                  40                  45

Phe Ser Thr Cys Asn Thr Pro Ala Gly Ala Lys Val Tyr Thr Ser Gly
    50                  55                  60

Arg Asp Gln Ile Lys Leu Pro Lys Gly Gln Ser Tyr Phe Ile Cys Asn
65              70                  75                  80

Phe Pro Gly His Cys Gln Ser Gly Met Lys Ile Ala Val Asn Ala Leu
                85                  90                  95
```

<210> SEQ ID NO 18
<211> LENGTH: 39
<212> TYPE: PRT
<213> ORGANISM: Neisseria gonnorrhoeae

<400> SEQUENCE: 18

```
Cys Ser Gln Glu Pro Ala Ala Pro Ala Ala Glu Ala Thr Pro Ala Gly
1               5                   10                  15

Glu Ala Pro Ala Ser Glu Ala Pro Ala Ala Glu Ala Ala Pro Ala Asp
            20                  25                  30

Ala Ala Glu Ala Pro Ala Ala
            35
```

<210> SEQ ID NO 19
<211> LENGTH: 166
<212> TYPE: PRT
<213> ORGANISM: Neisseria gonorrhoeae

<400> SEQUENCE: 19

```
Cys Ser Gln Glu Pro Ala Ala Pro Ala Ala Glu Ala Thr Pro Ala Gly
 1               5                  10                  15
Glu Ala Pro Ala Ser Glu Ala Pro Ala Ala Glu Ala Ala Pro Ala Asp
             20                  25                  30
Ala Ala Glu Ala Pro Ala Ala Gly Asn Cys Ala Ala Thr Val Glu Ser
         35                  40                  45
Asn Asp Asn Met Gln Phe Asn Thr Lys Asp Ile Gln Val Ser Lys Ala
 50                  55                  60
Cys Lys Glu Phe Thr Ile Thr Leu Lys His Thr Gly Thr Gln Pro Lys
 65                  70                  75                  80
Ala Ser Met Gly His Asn Leu Val Ile Ala Lys Ala Glu Asp Met Asp
                 85                  90                  95
Gly Val Phe Lys Asp Gly Val Gly Ala Ala Asp Thr Asp Tyr Val Lys
                100                 105                 110
Pro Asp Asp Ala Arg Val Val Ala His Thr Lys Leu Ile Gly Gly Gly
                115                 120                 125
Glu Glu Ser Ser Leu Thr Leu Asp Pro Ala Lys Leu Ala Asp Gly Asp
             130                 135                 140
Tyr Lys Phe Ala Cys Thr Phe Pro Gly His Gly Ala Leu Met Asn Gly
145                 150                 155                 160
Lys Val Thr Leu Val Asp
                165

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccggaattcc ggcagggatg ttgtaaatat ccg                                    33

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggggtaccgc cgtggcaggc atacagcatt tcaatcgg                               38

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggcagcaggg gcttcggcag catctgc                                           27

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 23
ctgcaggtcg actctagagg atcccg                                            26

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gccgagtgct cggtggacat ccagg                                             25

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tactcgagtc acttcagggt cagggtg                                           27

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgggatcccc ggcaacctgc cgaagaacgt catgggc                                37

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cggaattcgc atcacttcag ggtcaggg                                          28

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccaagctgat cggctcgtga gagaaggact cggtgacc                               38

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 29
ggtcaccgag tccttctctc acgagccgat cagcttgg                              38

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cggggatccc cggctcgggc gagaaggac                                        29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgggaattct ccacttcagg gtcagggtg                                        29

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gttcttctgc acctagccgg gccactccg                                        29

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cggagtggcc cggctaggtg cagaagaac                                        29
```